US010072094B2

(12) United States Patent
Lobb et al.

(10) Patent No.: US 10,072,094 B2
(45) Date of Patent: *Sep. 11, 2018

(54) COMPOSITIONS AND METHODS FOR TUMOR TRANSDUCTION

(71) Applicant: Aleta Biotherapeutics Inc., Natick, MA (US)

(72) Inventors: Roy Lobb, Wellesley, MA (US); Paul Rennert, Holliston, MA (US)

(73) Assignee: Aleta Biotherapeutics Inc., Natick, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/670,535

(22) Filed: Aug. 7, 2017

(65) Prior Publication Data

US 2018/0022821 A1 Jan. 25, 2018

Related U.S. Application Data

(63) Continuation of application No. 15/317,877, filed as application No. PCT/US2016/059578 on Oct. 28, 2016.

(60) Provisional application No. 62/249,183, filed on Oct. 30, 2015.

(51) Int. Cl.
| | |
|---|---|
| *C07K 16/32* | (2006.01) |
| *A61K 38/17* | (2006.01) |
| *A61K 39/395* | (2006.01) |
| *C07K 14/705* | (2006.01) |
| *C07K 14/71* | (2006.01) |
| *C07K 16/30* | (2006.01) |
| *A61K 47/68* | (2017.01) |
| *C12N 15/86* | (2006.01) |
| *A61K 47/64* | (2017.01) |
| *A61K 39/00* | (2006.01) |

(52) U.S. Cl.
CPC ............ *C07K 16/32* (2013.01); *A61K 38/177* (2013.01); *A61K 38/1774* (2013.01); *A61K 39/39558* (2013.01); *A61K 47/646* (2017.08); *A61K 47/6839* (2017.08); *C07K 14/70503* (2013.01); *C07K 14/70578* (2013.01); *C07K 14/71* (2013.01); *C07K 16/30* (2013.01); *C12N 15/86* (2013.01); *A61K 2039/507* (2013.01); *C07K 2317/622* (2013.01); *C07K 2317/732* (2013.01); *C07K 2319/74* (2013.01); *C12N 2750/14143* (2013.01)

(58) Field of Classification Search
None
See application file for complete search history.

(56) References Cited

U.S. PATENT DOCUMENTS

| | | |
|---|---|---|
| 5,994,136 A | 11/1999 | Naldini et al. |
| 6,165,782 A | 12/2000 | Naldini et al. |
| 6,326,193 B1 | 12/2001 | Liu et al. |
| 6,416,945 B1 | 7/2002 | McCarthy et al. |
| 6,428,953 B1 | 8/2002 | Naldini et al. |
| 6,599,739 B1 | 7/2003 | Lowy et al. |
| 7,205,126 B2 | 4/2007 | Qiao et al. |
| 8,394,411 B2 | 3/2013 | Roberts et al. |
| 8,470,528 B2 | 6/2013 | Pasqualini et al. |
| 2006/0205069 A1 | 9/2006 | June et al. |
| 2013/0089539 A1 | 4/2013 | Rennert et al. |
| 2014/0099309 A1 | 4/2014 | Powell, Jr. et al. |
| 2017/0260288 A1 | 9/2017 | Lobb et al. |

FOREIGN PATENT DOCUMENTS

| | | |
|---|---|---|
| EP | 1697421 B1 | 9/2010 |
| WO | WO-98/37186 A1 | 8/1998 |
| WO | WO-01/29058 A1 | 4/2001 |
| WO | WO-01/96584 A2 | 12/2001 |
| WO | WO-2015/007542 A1 | 1/2015 |
| WO | WO-2017/075533 | 5/2017 |

OTHER PUBLICATIONS

Yu, et al. (earliest date published online: Oct. 17, 2013) "T-cell Engager-armed Oncolytic Vaccinia Virus Significantly Enhances Antitumor Therapy", Molecular Therapy, 22(1): 102-11.*
Dong, et al. (Sep. 17, 2014 online) "ORCA-010 a Novel Potency-Enhanced Oncolytic Adenovirus, Exerts Strong Antitumor Activity in Preclinical Models", Human Gene Therapy, 25(10): 897-904.*
Baas, Tracey, Keys to the CAR, SciBX: Science-Business eXchange, 7 pages (2014).
Biragyn, A. et al., Genetic fusion of chemokines to a self tumor antigen induces protective, T-cell dependent antitumor immunity, Nature Biotechnology, 17:253-258 (1999).
Boder, E. and Wittrup, K., Yeast surface display for screening combinatorial polypeptide libraries, Nat Biotechnol, 15:553-557 (1997).
Bouchard, H., Antibody-drug conjugates—a new wave of cancer drugs, Bioorg Med Chem Lett, 24(23):5357-63 (2014).
Buck, CB and Thompson, CD, Production of papillomavirus-based gene transfer vectors, Curr Protoc Cell Biol, Chapter 26:Unit 26.1 (2007).
Colombo, M. and Trinchieri, G., Interleukin-12 in anti-tumor immunity and immunotherapy, Cytokine Growth Factor Rev, 13(2):155-68 (2002).
Conlon, K. et al., Redistribution, hyperproliferation, activation of natural killer cells and CD8 T cells, and cytokine production during first-in-human clinical trial of recombinant human interleukin-15 in patients with cancer, J Clin Oncol, 33(1):74-82 (2015).

(Continued)

*Primary Examiner* — Robert M Kelly
(74) *Attorney, Agent, or Firm* — Choate, Hall & Stewart LLP; Brenda Herschbach Jarrell; Rolando Medina

(57) ABSTRACT

The invention relates to cancer therapeutics, in particular, the system of making cancer cells more susceptible to effector cells by introduction of cellular therapy targets into the cancer cells.

28 Claims, 6 Drawing Sheets

Specification includes a Sequence Listing.

(56) References Cited

OTHER PUBLICATIONS

Cull, M. et al., Screening for receptor ligands using large libraries of peptides linked to the C terminus of the lac repressor, Proc Natl Acad Sci USA, 89(5):1865-9 (1992).
Czerkinsky, C. et al., A Solid-Phase Enzyme-Linked Immunospot (ELISPOT) Assay for Enumeration of Specific Antibody-Secreting Cells, Journal of Immunological Methods, 65:109-121 (1983).
Dreher, M. et al., Colony assays for antibody fragments expressed in bacteria, J Immunol Methods, 139(2):197-205 (1991).
Fuchs, P. et al., Targeting recombinant antibodies to the surface of *Escherichia coli*: fusion to a peptidoglycan associated lipoprotein, Biotechnology (NY), 9(12):1369-72 (1991).
Gevaert, K. and Vandekerckhove, J., Protein identification methods in proteomics, Electrophoresis, 21(6):1145-54 (2000).
Grabherr, R. and Ernst, W., The baculovirus expression system as a tool for generating diversity by viral surface display, Comb Chem High Throughput Screen, 4(2):185-92 (2001).
Guthals, A. et al., Shotgun protein sequencing with meta-contig assembly, Mol Cell Proteomics, 11(10):1084-96 (2012).
Hajitou, A. et al., A Hybrid Vector for Ligand-Directed Tumor Targeting and Molecular Imaging, Cell, 125:385-398 (2006).
Hung, C. et al., Ovarian cancer gene therapy using HPV-16 pseudovirion carrying the HSV-tk gene, PLoS One, 7(7):e40983 (2012).
International Search Report for PCT/US2016/059578, 4 pages (dated Jan. 30, 2017).
Kang, A.S. et al., Linkage of recognition and replication functions by assembling combinatorial antibody Fab libraries along phage surfaces, Proc Natl Acad Sci USA, 88:4363-4366 (1991).
Kines, R. et al., Human papillomavirus capsids preferentially bind and infect tumor cells, International Journal of Cancer, 138:901-911 (2016).
Kontermann, R., Dual targeting strategies with bispecific antibodies, Mabs, 4(2):182-197 (2012).
Leonard, J. et al., Effects of single-dose interleukin-12 exposure on interleukin-12-associated toxicity and interferon-gamma production, Blood, 90(7):2541-2548 (1997).
Papadakis, E. et al., Promoters and control elements: designing expression cassettes for gene therapy, Curr Gene Ther, 4(1):89-113 (2004).
Roberts, R. and Szostak, J., RNA-peptide fusions for the in vitro selection of peptides and proteins, Proc Natl Acad Sci USA, 94(23):12297-302 (1997).
Sassoon, I. and Blanc, V., Antibody-drug conjugate (ADC) clinical pipeline: a review, Methods Mol Biol, 1045:1-27 (2013).
Schaffitzel, C. et al., Ribosome display: an in vitro method for selection and evolution of antibodies from libraries, J Immunol Methods, 231(1-2):119-35 (1999).
Tedder, TF., CD19: a promising B cell target for rheumatoid arthritis, Nat Rev Rheumatol, 5(10):572-577 (2009).
Tugues, S., et al., New insights into IL-12-mediated tumor suppression, Cell Death Differ, 22(2):237-46 (2015).
Wang, K., et al., CD19: a biomarker for B cell development, lymphoma diagnosis and therapy, Exp Hematol Oncol, 1(1):36, 7 pages (2012).
Written Opinion for PCT/US2016/059578, 8 pages (dated Jan. 30, 2017).
Sorensen, E. et al., IL-12 Suppresses Vascular Endothelial Growth Factor Receptor 3 Expression on Tumor Vessels by Two Distinct IFN-γ-Dependent Mechanisms, J. Immunol, 184:1858-1866 (2010).

\* cited by examiner

SEQUENCE LISTING

<160> NUMBER OF SEQ ID NOS: 8

<210> SEQ ID NO 1
<211> LENGTH: 553
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp

```
                   20                  25                  30
Asn Ala Val Leu Gln Cys Leu Lys Gly Thr Ser Asp Gly Pro Thr Gln
             35                  40                  45
Gln Leu Thr Trp Ser Arg Glu Ser Pro Leu Lys Pro Phe Leu Lys Leu
 50                  55                  60
Ser Leu Gly Leu Pro Gly Leu Gly Ile His Met Arg Pro Leu Ala Ile
 65                  70                  75                  80
Trp Leu Phe Ile Phe Asn Val Ser Gln Gln Met Gly Gly Phe Tyr Leu
                 85                  90                  95
Cys Gln Pro Gly Pro Pro Ser Glu Lys Ala Trp Gln Pro Gly Trp Thr
                100                 105                 110
Val Asn Val Glu Gly Ser Gly Glu Leu Phe Arg Trp Asn Val Ser Asp
            115                 120                 125
Leu Gly Gly Leu Gly Cys Gly Leu Lys Asn Arg Ser Ser Glu Gly Pro
            130                 135                 140
Ser Ser Pro Ser Gly Lys Leu Met Ser Pro Lys Leu Tyr Val Trp Ala
145                 150                 155                 160
Lys Asp Arg Pro Glu Ile Trp Glu Gly Glu Pro Pro Cys Leu Pro Pro
                165                 170                 175
Arg Asp Ser Leu Asn Gln Ser Leu Ser Gln Asp Leu Thr Met Ala Pro
            180                 185                 190
Gly Ser Thr Leu Trp Leu Ser Cys Gly Val Pro Pro Asp Ser Val Ser
            195                 200                 205
Arg Gly Pro Leu Ser Trp Thr His Val His Pro Lys Gly Pro Lys Ser
            210                 215                 220
Leu Leu Ser Leu Glu Leu Lys Asp Asp Arg Pro Ala Arg Asp Met Trp
225                 230                 235                 240
Val Met Glu Thr Gly Leu Leu Leu Pro Arg Ala Thr Ala Gln Asp Ala
                245                 250                 255
Gly Lys Tyr Tyr Cys His Arg Gly Asn Leu Thr Met Ser Phe His Leu
                260                 265                 270
Glu Ile Thr Ala Arg Pro Gly Gly Gly Gly Ser Gly Gly Gly Gly Ser
            275                 280                 285
Gly Gly Gly Gly Ser Gly Gly Gly Gly Ser Glu Val Gln Leu Val Glu
            290                 295                 300
Ser Gly Gly Gly Leu Val Gln Pro Gly Gly Ser Leu Arg Leu Ser Cys
305                 310                 315                 320
Ala Ala Ser Gly Phe Asn Ile Lys Asp Thr Tyr Ile His Trp Val Arg
                325                 330                 335
Gln Ala Pro Gly Lys Gly Leu Glu Trp Val Ala Arg Ile Tyr Pro Thr
            340                 345                 350
Asn Gly Tyr Thr Arg Tyr Ala Asp Ser Val Lys Gly Arg Phe Thr Ile
            355                 360                 365
Ser Ala Asp Thr Ser Lys Asn Thr Ala Tyr Leu Gln Met Asn Ser Leu
            370                 375                 380
Arg Ala Glu Asp Thr Ala Val Tyr Tyr Cys Ser Arg Trp Gly Gly Asp
385                 390                 395                 400
Gly Phe Tyr Ala Met Asp Tyr Trp Gly Gln Gly Thr Leu Val Thr Val
                405                 410                 415
Ser Ser Ala Ser Thr Gly Gly Gly Ser Gly Gly Gly Gly Ser Gly
            420                 425                 430
Gly Gly Gly Ser Asp Ile Gln Met Thr Gln Ser Pro Ser Ser Leu Ser
            435                 440                 445
```

```
Ala Ser Val Gly Asp Arg Val Thr Ile Thr Cys Arg Ala Ser Gln Asp
    450                 455                 460

Val Asn Thr Ala Val Ala Trp Tyr Gln Gln Lys Pro Gly Lys Ala Pro
465                 470                 475                 480

Lys Leu Leu Ile Tyr Ser Ala Ser Phe Leu Tyr Ser Gly Val Pro Ser
                485                 490                 495

Arg Phe Ser Gly Ser Arg Ser Gly Thr Asp Phe Thr Leu Thr Ile Ser
            500                 505                 510

Ser Leu Gln Pro Glu Asp Phe Ala Thr Tyr Tyr Cys Gln Gln His Tyr
        515                 520                 525

Thr Thr Pro Pro Thr Phe Gly Gln Gly Thr Lys Val Glu Ile Lys Arg
    530                 535                 540

Thr Ser Arg His His His His His His
545                 550

<210> SEQ ID NO 2
<211> LENGTH: 1659
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
atgccacctc ctcgcctcct cttcttcctc ctcttcctca cccccatgga agtcaggccc      60
gaggaacctc tagtggtgaa ggtggaagag ggagataacg ctgtgctgca gtgcctcaag     120
gggacctcag atggccccac tcagcagctg acctggtctc gggagtcccc gcttaaaccc     180
ttcttaaaac tcagcctggg gctgccaggc ctgggaatcc acatgaggcc cctggccatc     240
tggcttttca tcttcaacgt ctctcaacag atgggggggct tctacctgtg ccagccgggg     300 ccccccctg agaaggcctg gcagcctggc tggacagtca atgtggaggg cagcggggag     360
ctgttccggt ggaatgtttc ggacctaggt ggcctgggct gtggcctgaa gaacaggtcc     420
tcagagggcc ccagctcccc ttccgggaag ctcatgagcc caagctgta tgtgtgggcc     480 aaagaccgcc ctgagatctg ggaggagag cctccgtgtc tcccaccgag ggacagcctg     540
aaccagagcc tcagccagga cctcaccatg gcccctggct ccacactctg gctgtcctgt     600
ggggtacccc ctgactctgt gtccaggggc ccctctcct ggacccatgt gcaccccaag     660
gggcctaagt cattgctgag cctagagctg aaggacgatc gccggccag agatatgtgg     720 gtaatggaga cgggtctgtt gttgcccggg gccacagctc aagacgctgg aaagtattat     780
tgtcaccgtg gcaacctgac catgtcattc cacctggaga tcactgctcg gccaggggga     840
ggtgggtctg gaggtggagg atctggtgga ggtgggtctg gtggaggtgg gtctgaggtg     900
cagctggtgg agtctggtgg tggtcttgtt caacctggtg gttctcttcg tctttcttgt     960
gctgcttctg gttttaatat taaagatact tatattcatt gggttcgtca agctcctggt    1020
aaaggtcttg aatgggttgc tcgtatttat cctactaatg gttatactcg ttatgctgat    1080
tctgttaaag gtcgttttac tatttctgct gatacttcta aaaatactgc ttatcttcaa    1140
atgaactctc ttcgtgctga agatactgct gtttattatt gttctcgttg gggtggtgat    1200 ggttttttatg ctatggatta ttggggtcaa ggtactcttg tcaccgtctc ctcagctagc    1260 accggggag gtgggtctgg aggtggagga tctggtggag gtgggtctga catccagatg    1320
acccagtctc cttcttctct ttctgcttct gttggtgatc gtgttactat tacttgtcgt    1380
```

```
gcttctcaag atgttaatac tgctgttgct tggtatcaac aaaaacctgg taaagctcct      1440
aaacttctta tttattctgc ttcttttctt tattctggtg ttccttctcg tttttctggt      1500
tctcgttctg gtactgattt tactcttact atttcttctc ttcaacctga agattttgct      1560
acttattatt gtcaacaaca ttatactact cctcctactt ttggtcaagg taccaaggtg      1620
gagatcaaac gtacgtctag acatcatcac catcaccat                            1659
```

<210> SEQ ID NO 3
<211> LENGTH: 557
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Gly Gly Gly Ser Gly Gly Gly Ser
            275                 280                 285

Gly Gly Gly Gly Ser Gly Gly Gly Ser Gln Val Gln Leu Val Gln
        290                 295                 300

Ser Gly Ala Glu Asp Lys Lys Pro Gly Glu Ser Val Lys Ile Ser Cys
```

```
                305                 310                 315                 320
Lys Ala Ser Gly Tyr Thr Phe Thr Asn Tyr Gly Met Asn Trp Val Arg
                    325                 330                 335
Gln Ala Pro Gly Gln Gly Leu Lys Trp Met Gly Trp Ile Asn Thr Tyr
                340                 345                 350
Thr Gly Glu Ser Thr Tyr Ala Asp Asp Phe Lys Gly Arg Phe Ala Phe
            355                 360                 365
Ser Leu Asp Thr Ser Ala Ser Thr Ala Tyr Leu Gln Leu Ser Ser Leu
        370                 375                 380
Arg Gly Glu Asp Thr Ala Val Tyr Phe Cys Ala Arg Phe Ala Ile Lys
385                 390                 395                 400
Gly Asp Tyr Trp Gly Gln Gly Thr Thr Val Thr Val Ser Ser Ala Ser
                405                 410                 415
Thr Gly Gly Gly Ser Gly Gly Gly Ser Gly Gly Gly Ser
                420                 425                 430
Gly Gly Gly Gly Ser Asp Ile Val Met Thr Gln Ser Pro Leu Ser Leu
            435                 440                 445
Glu Val Ser Pro Gly Glu Pro Ala Ser Ile Ser Cys Arg Ser Thr Lys
        450                 455                 460
Ser Leu Leu His Ser Asp Gly Ile Thr Tyr Leu Tyr Trp Tyr Leu Gln
465                 470                 475                 480
Lys Pro Gly Gln Ser Pro Gln Leu Leu Ile Tyr Gln Leu Ser Asn Leu
                485                 490                 495
Ala Ser Gly Val Pro Asp Arg Phe Ser Ser Ser Gly Ser Gly Thr Asp
            500                 505                 510
Phe Thr Leu Lys Ile Ser Arg Val Glu Ala Glu Asp Glu Gly Thr Tyr
        515                 520                 525
Tyr Cys Ala Gln Asn Leu Glu Ile Pro Arg Thr Phe Gly Gln Gly Thr
    530                 535                 540
Lys Leu Glu Ile Lys Arg Thr His His His His His
545                 550                 555

<210> SEQ ID NO 4
<211> LENGTH: 1671
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
atgccacctc ctcgcctcct cttcttcctc ctcttcctca cccccatgga agtcaggccc      60
gaggaacctc tagtggtgaa ggtggaagag ggagataacg ctgtgctgca gtgcctcaag     120
gggacctcag atggccccac tcagcagctg acctggtctc gggagtcccc gcttaaaccc     180
ttcttaaaac tcagcctggg gctgccaggc ctgggaatcc acatgaggcc cctggccatc     240
tggcttttca tcttcaacgt ctctcaacag atgggggct tctacctgtg ccagccgggg     300 ccccctctg agaaggcctg gcagcctggc tggacagtca atgtggaggg cagcggggag     360
ctgttccggt ggaatgtttc ggacctaggt ggcctgggct gtggcctgaa gaacaggtcc     420
tcagagggcc ccagctcccc ttccgggaag ctcatgagcc caagctgta tgtgtgggcc     480 aaagaccgcc tgagatctgg gagggagag cctccgtgtc tcccaccgag ggacagcctg     540
aaccagagcc tcagccagga cctcaccatg gccctggct ccacactctg ctgtcctgt      600 ggggtacccc ctgactctgt gtccaggggc ccctctcct ggacccatgt gcaccccaag     660
```

-continued

```
gggcctaagt cattgctgag cctagagctg aaggacgatc gcccggccag agatatgtgg      720
gtaatggaga cgggtctgtt gttgccccgg gccacagctc aagacgctgg aaagtattat      780
tgtcaccgtg caacctgac catgtcattc cacctggaga tcactgctcg gccaggagga      840
ggtgggtctg gaggtggagg atctggtgga ggtgggtctg gaggaggtgg gtctcaggtg      900
cagctggtgc agagcggcgc cgaggacaag aagcccggcg agagcgtgaa gatcagctgc      960
aaggccagcg gctacacctt caccaactac ggcatgaact gggtgaggca ggcccccggc     1020
cagggcctga agtggatggg ctggatcaac acctacaccg gcgagagcac ctacgccgac     1080
gacttcaagg gcaggttcgc cttcagcctg gacaccagcg ccagcaccgc ctacctgcag     1140
ctgagcagcc tgagggcga ggacaccgcc gtgtacttct gcgccaggtt cgccatcaag      1200
ggcgactact ggggccaggg caccaccgtg accgtgagca gcgccagcac cggcggcggc     1260
ggcagcggcg gcggcggcag cggcggcggc ggcagcggcg gcggcggcag cgacatcgtg     1320
atgacccaga gccccctgag cctggaggtg agccccggcg agcccgccag catcagctgc     1380
aggagcacca gagcctgct gcacagcgac ggcatcacct acctgtactg gtacctgcag      1440
aagcccggcc agagccccca gctgctgatc taccagctga gcaacctggc cagcggcgtg     1500
cccgacaggt tcagcagcag cggcagcggc accgacttca ccctgaagat cagcagggtg     1560
gaggccgagg acgagggcac ctactactgc gcccagaacc tggagatccc caggaccttc     1620
ggccagggca ccaagctgga gatcaagagg acccatcatc accatcacca t              1671
```

<210> SEQ ID NO 5
<211> LENGTH: 552
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 5

```
Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175
```

```
Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Gly Gly Gly Ser Gly Gly Gly Gly Ser
        275                 280                 285

Gly Gly Gly Gly Ser Gly Gly Gly Ser Gln Val Gln Leu Val Gln
        290                 295                 300

Ser Gly Ala Glu Asp Val Lys Pro Asp Ala Ser Val Lys Leu Ser Cys
305                 310                 315                 320

Lys Ala Ser Gly Tyr Thr Phe Thr Asp Tyr Tyr Met His Trp Val Arg
                325                 330                 335

Gln Ala Pro Gly Gln Gly Leu Glu Trp Met Gly Arg Val Asn Pro Asn
            340                 345                 350

Arg Arg Gly Thr Thr Tyr Asn Gln Lys Phe Glu Gly Arg Val Thr Met
        355                 360                 365

Thr Thr Asp Thr Ser Thr Ser Thr Ala Tyr Met Gln Leu Ser Ser Leu
    370                 375                 380

Arg Gly Glu Asp Thr Ala Val Tyr Tyr Cys Ala Arg Ala Asn Trp Leu
385                 390                 395                 400

Asp Tyr Trp Gly Gln Gly Thr Thr Val Thr Val Ser Ser Ala Ser Thr
                405                 410                 415

Gly Gly Gly Gly Ser Gly Gly Gly Ser Gly Gly Gly Gly Ser Gly
            420                 425                 430

Gly Gly Gly Ser Asp Ile Gln Met Thr Gln Ser Pro Ser Ser Leu Glu
        435                 440                 445

Ala Ser Val Gly Asp Arg Val Thr Ile Thr Cys Ser Val Ser Ser Ser
450                 455                 460

Val Ser Ser Ile Tyr Leu His Trp Tyr Gln Gln Lys Pro Gly Lys Ser
465                 470                 475                 480

Pro Lys Leu Leu Ile Tyr Ser Thr Ser Asn Leu Ala Ser Gly Val Pro
                485                 490                 495

Asp Arg Phe Ser Gly Ser Gly Ser Gly Thr Asp Phe Thr Leu Thr Ile
            500                 505                 510

Ser Ser Leu Gln Ala Glu Asp Glu Gly Thr Tyr Tyr Cys Gln Val Tyr
        515                 520                 525

Ser Gly Tyr Pro Leu Thr Phe Gly Gly Gly Thr Lys Leu Glu Ile Lys
    530                 535                 540

Arg Thr His His His His His His
545                 550
```

<210> SEQ ID NO 6
<211> LENGTH: 1656
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6

```
atgccacctc ctcgcctcct cttcttcctc ctcttcctca cccccatgga agtcaggccc      60
gaggaacctc tagtggtgaa ggtggaagag ggagataacg ctgtgctgca gtgcctcaag     120
gggacctcag atggccccac tcagcagctg acctggtctc gggagtcccc gcttaaaccc     180
ttcttaaaac tcagcctggg gctgccaggc ctgggaatcc acatgaggcc cctgccatc     240
tggctttca tcttcaacgt ctctcaacag atgggggct tctacctgtg ccagccgggg      300
cccccctctg agaaggcctg gcagcctggc tggacagtca atgtggaggg cagcggggag     360
ctgttccggt ggaatgtttc ggacctaggt ggcctgggct gtggcctgaa gaacaggtcc     420
tcagagggcc ccagctcccc ttccgggaag ctcatgagcc caagctgta tgtgtgggcc     480
aaagaccgcc ctgagatctg ggaggagag cctccgtgtc tcccaccgag ggacagcctg     540
aaccagagcc tcagccagga cctcaccatg gccctggct ccacactctg gctgtcctgt     600
ggggtacccc ctgactctgt gtccaggggc cccctctcct ggacccatgt gcaccccaag     660
gggcctaagt cattgctgag cctagagctg aaggacgatc gcccggccag agatatgtgg     720
gtaatggaga cgggtctgtt gttgccccgg ccacagctc aagacgctgg aaagtattat     780
tgtcaccgtg caacctgac catgtcattc cacctggaga tcactgctcg gccaggagga     840
ggtgggtctg gaggtggagg atctggtgga ggtgggtctg gaggagggtgg gtctcaggtt     900
cagctggtgc agtctggtgc tgaggatgtg aagcctgatg cctcagtgaa gctctcctgc     960
aaggcttctg gttacacatt cactgactac tacatgcact gggtgcgtca ggccctggt     1020
caaggtcttg agtggatggg tcgtgttaat cctaaccgga ggggtactac ctacaaccag    1080
aaattcgagg gccgtgtcac catgaccaca gacacatcca cgagcacagc ctacatgcag    1140
ctgagtagcc tgcgtggtga agacacggcc gtgtattact gtgcgcgtgc gaactggctt    1200
gactactggg gccagggcac caccgtcacc gtctcctccg cctccaccgg ggaggtgggg    1260
tctggaggtg gaggatctgg tggaggtggg tctggtggag gtgggtctga catccagatg    1320
acccagtctc catcctccct ggaggcatct gtaggagaca gagtcaccat cacttgcagt    1380
gtcagctcaa gtgtatcctc catttacttg cactggtatc agcagaaacc agggaaaagc    1440
cctaagctcc tgatctatag cacatccaac ttggcttctg gagtcccaga taggttcagt    1500
ggcagtggat ctgggacaga tttcactctc accatcagca gtctgcaagc cgaagatgag    1560
ggcacttact actgtcaagt ctacagtggt tacccgctca cgttcggcgg agggaccaag    1620
ctggagatca aacgaactca tcatcaccat caccat                              1656
```

<210> SEQ ID NO 7
<211> LENGTH: 555
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 7

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
     50                  55                  60

Ser Leu Gly Leu Pro Gly Leu Gly Ile His Met Arg Pro Leu Ala Ile
65                   70                  75                  80

Trp Leu Phe Ile Phe Asn Val Ser Gln Gln Met Gly Gly Phe Tyr Leu
                     85                  90                  95

Cys Gln Pro Gly Pro Pro Ser Glu Lys Ala Trp Gln Pro Gly Trp Thr
             100                 105                 110

Val Asn Val Glu Gly Ser Gly Glu Leu Phe Arg Trp Asn Val Ser Asp
         115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Gly Gly Gly Ser Gly Gly Gly Gly Ser
        275                 280                 285

Gly Gly Gly Gly Ser Gly Gly Gly Ser Gln Val Gln Leu Gln Glu
    290                 295                 300

Ser Gly Pro Gly Asp Val Lys Pro Ser Glu Thr Leu Ser Leu Thr Cys
305                 310                 315                 320

Thr Val Ser Gly Gly Ser Val Ser Ser Gly Asp Tyr Tyr Trp Thr Trp
                325                 330                 335

Ile Arg Gln Ser Pro Gly Lys Gly Leu Glu Trp Ile Gly His Ile Tyr
            340                 345                 350

Tyr Ser Gly Asn Thr Asn Tyr Asn Pro Ser Leu Lys Ser Arg Leu Thr
        355                 360                 365

Ile Ser Ile Asp Thr Ser Lys Thr Thr Phe Ser Leu Gln Leu Ser Ser
    370                 375                 380

Val Thr Gly Glu Asp Thr Ala Ile Tyr Tyr Cys Val Arg Asp Arg Val
385                 390                 395                 400

Thr Gly Ala Phe Asp Ile Trp Gly Gln Gly Thr Val Thr Val Ser
                405                 410                 415

Ser Ala Ser Thr Gly Gly Gly Gly Ser Gly Gly Gly Ser Gly Gly
            420                 425                 430

Gly Gly Ser Gly Gly Gly Gly Ser Asp Ile Gln Met Thr Gln Ser Pro
        435                 440                 445

Ser Ser Leu Glu Ala Ser Val Gly Asp Arg Val Thr Ile Thr Cys Gln
    450                 455                 460

Ala Ser Gln Asp Ile Ser Asn Tyr Leu Asn Trp Tyr Gln Gln Lys Pro
465                 470                 475                 480

Gly Lys Ser Pro Lys Leu Leu Ile Tyr Asp Ala Ser Asn Leu Glu Thr
                485                 490                 495

Gly Val Pro Asp Arg Phe Ser Gly Ser Gly Ser Gly Thr Asp Phe Thr
            500                 505                 510

Phe Thr Ile Ser Ser Leu Gln Ala Glu Asp Glu Gly Thr Tyr Phe Cys
        515                 520                 525

Gln His Phe Asp His Leu Pro Leu Ala Phe Gly Gly Gly Thr Lys Leu
    530                 535                 540

Glu Ile Lys Arg Thr His His His His His His
545                 550                 555

<210> SEQ ID NO 8
<211> LENGTH: 1665
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
atgccacctc ctcgcctcct cttcttcctc ctcttcctca cccccatgga agtcaggccc     60
gaggaacctc tagtggtgaa ggtggaagag ggagataacg ctgtgctgca gtgcctcaag    120
gggacctcag atggccccac tcagcagctg acctggtctc gggagtcccc gcttaaaccc    180
ttcttaaaac tcagcctggg gctgccaggc ctgggaatcc acatgaggcc cctggccatc    240
tggcttttca tcttcaacgt ctctcaacag atgggggggct tctacctgtg ccagccgggg    300 ccccccctctg agaaggcctg gcagcctggc tggacagtca atgtggaggg cagcggggag    360
ctgttccggt ggaatgtttc ggacctaggt ggcctgggct gtggcctgaa aacaggtcc    420 tcagagggcc ccagctcccc ttccgggaag ctcatgagcc caagctgta tgtgtgggcc    480 aaagaccgcc ctgagatctg ggaggagag cctccgtgtc tcccaccgag ggacagcctg    540
aaccagagcc tcagccagga cctcaccatg gcccctggct ccacactctg gctgtcctgt    600
ggggtacccc ctgactctgt gtccaggggc ccctctcct ggacccatgt gcaccccaag    660
gggcctaagt cattgctgag cctagagctg aaggacgatc gccggccag agatatgtgg    720 gtaatggaga cgggtctgtt gttgcccgg gccacagctc aagacgctgg aaagtattat    780
tgtcaccgtg caacctgac catgtcattc cacctggaga tcactgctcg gccaggagga    840
ggtgggtctg gaggtggagg atctggtgga ggtgggtctg gaggaggtgg gtctcaggtg    900
cagctgcagg agagcggccc cggcgacgtg aagcccagcg agaccctgag cctgacctgc    960
accgtgagcg gcgcagcgt gagcagcggc gactactact ggacctggat caggcagagc   1020
cccggcaagg gcctggagtg gatcggccac atctactaca gcggcaacac caactacaac   1080
cccagcctga gagcaggct gaccatcagc atcgacacca agaccac cttcagcctg   1140 cagctgagca gcgtgaccgg cgaggacacc gccatctact actgcgtgag ggacagggtg   1200
accggcgcct tcgacatctg gggccagggc accaccgtga ccgtgagcag cgccagcacc   1260
ggcggcggcg gcagcggcgg cggcggcagc ggcggcggcg gcagcggcgg cggcggcagc   1320
gacatccaga tgacccagag ccccagcagc ctggaggcca gcgtgggcga cagggtgacc   1380
atcacctgcc aggccagcca ggacatcagc aactacctga actggtacca gcagaagccc   1440
ggcaagagcc ccaagctgct gatctacgac gccagcaacc tggagaccgg cgtgcccgac   1500

```
aggttcagcg gcagcggcag cggcaccgac ttcaccttca ccatcagcag cctgcaggcc    1560
gaggacgagg gcacctactt ctgccagcac ttcgaccacc tgcccctggc cttcggcggc    1620
ggcaccaagc tggagatcaa gaggacccat catcaccatc accat                    1665
```

COMPOSITIONS AND METHODS FOR TUMOR TRANSDUCTION

CROSS REFERENCE TO RELATED APPLICATIONS

This application is a continuation application of U.S. non-provisional application Ser. No. 15/317,877, filed Dec. 9, 2016, which is the National Stage Entry of International Application No. PCT/US2016/059578 which claims priority to U.S. Provisional Patent Application No. 62/249,183 filed Oct. 30, 2015, the entire contents of which is hereby incorporated by reference.

SEQUENCE LISTING

In accordance with 37 CFR 1.52(e)(5), the present specification makes reference to a Sequence Listing submitted electronically in the form of a text file (entitled "2012106-0008_SL.txt", created on Nov. 17, 2016 and is 29,112 bytes in size) the entire contents of which are incorporated herein by reference in their entirety.

BACKGROUND OF THE INVENTION

Recent examples of chimeric antigen receptor (CAR) T cell directed to solid tumors have been clinical (or even preclinical) failures. The invention described herein presents solutions for solid tumor and other oncology indications.

Cellular therapeutics that are introduced into cancer patients and traffic into tumor microenvironments encounter multiple barriers that limit their efficacy. These barriers include, but are not limited to: cellular anergy, intrinsic cell death, suboptimal cell trafficking, limited proliferation, limited effector function, poor "take" (survival, persistence and differentiation), active exclusion from tumors, persistent immunosuppression in the tumor microenvironment, and tumor-induced cell death. Almost all attempts to date to overcome these limitations require non-physiological manipulation of the cellular therapeutic both in vitro and in vivo. The efficacy of cellular therapeutics is therefore broadly hindered by both intrinsic and extrinsic factors.

Targeting solid tumors presents an additional set of challenges to overcome, for example, their overall lesser sensitivity to T cell mediated cytotoxicity, a microenvironment with differing immunosuppressive mechanisms between tumor types, and a lack of target antigens with favorable expression profiles. Additionally, solid tumors are heavily fortified against cellular therapeutic attack as they deploy an impenetrable extracellular matrix, hypoxia, and acidic pH. Despite the vast number of targets that have been investigated, only a small number are tumor-specific (e.g., expression is restricted to the tumor cell) and this finding, as such, illustrates the difficulty and the need to discover an effective solution for eliminating or reducing the tumor. Yet another problem for targeting tumors is the heterogeneity of the tumor cells which express different antigens and different levels of antigens. The invention described herein addresses these problems and provides additional benefits as well.

SUMMARY OF THE INVENTION

The present invention is based, at least in part, upon the introduction of cellular therapy targets into cancer cells (e.g., tumor cells such as solid tumor cells) such that they are more susceptible to effector cells that can eliminate and/or reduce the cancer cells. As further detailed herein, cancer cells (e.g., tumors) can be transduced with fusion proteins. Such fusion proteins consist of a binding component fused to a target component. For example, the fusion protein can be an antibody or antibody fragment which binds to one or more tumor-associated antigens (TAA) or tumor-specific antigens (TSA), fused to a target for cellular therapy, e.g. CD19; a cytokine-target fusion; a bi-specific T-cell engager (BiTE). They can also be transduced with CD19 variants (or mutants). These fusion proteins or variants (or mutants) can be secreted by the tumor cells and/or permeate the tumor microenvironment.

Accordingly, in one aspect, the invention provides for recombinant vectors encoding an antibody or antibody fragment to a tumor-associated antigens (TAA) or tumor-specific antigens (TSA) and a therapeutic agent, as a fusion protein. In other embodiments, the therapeutic agent is selected from the group consisting of a cytokines, peptides, proteins, antibodies, antibody fragments, T-cell engager and NK-cell engager. In other embodiments, the therapeutic agent is selected from the group consisting of glioma-associated antigen, carcinoembryonic antigen (CEA), β-human chorionic gonadotropin, alphafetoprotein (AFP), lectin-reactive AFP, thyroglobulin, RAGE-1, MN-CA IX, human telomerase reverse transcriptase, RU1, RU2(AS), intestinal carboxyl esterase, mut hsp70-2, M-CSF, prostase, prostate-specific antigen (PSA), PAP, NY-ESO-1, LAGE-la, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin, EphA2, HER2, GD2, Glypican-3, 5T4, 8H9, αvβ6 integrin, BCMA, B7-H3, B7-H6, CAIX, CA9, CD19, CD20, CD22, kappa light chain, CD30, CD33, CD38, CD44, CD44v6, CD44v7/8, CD70, CD123, CD138, CD171, CEA, CSPG4, EGFR, EGFRvIII, EGP2, EGP40, EPCAM, ERBB3, ERBB4, ErbB3/4, FAP, FAR, FBP, fetal AchR, Folate Receptor a, GD2, GD3, HLA-AI MAGE Al, HLA-A2, IL1 1Ra, IL13Ra2, KDR, Lambda, Lewis-Y, MCSP, Mesothelin, Mucl, Mucl6, NCAM, NKG2D ligands, NY-ESO-1, PRAME, PSCA, PSC1, PSMA, ROR1, SURVIVIN, TAG72, TEM1, TEM8, VEGRR2, carcinoembryonic antigen, HMW-MAA, and VEGF receptors.

In other embodiments, the cytokine is capable of being secreted by a tumor cell comprising said vector. In other embodiments, the vector is a viral vector. In other embodiments, the vector integrates into the genome of a cancer cell. In other embodiments, the therapeutic agent is an antigen is an antigen for a chimeric antigen receptor (CAR). In other embodiments, the therapeutic agent is an antigen for a T cell receptor (TCR). In other embodiments, the therapeutic agent is an antigen for an ADC antibody, ADCC antibody, and/or a radiotherapeutic antibody. In other embodiments, the therapeutic agent is an immunostimulatory cytokine or molecule selected from the group consisting of TLR agonists, PAMP, DAMP and other stimulators. In other embodiments, the therapeutic agent is a peptide with immunomodulatory or anti-tumor properties. In other embodiments, the TAA or TSA and therapeutic agent are expressed as a fusion protein. In other embodiments, the TAA or TSA is selected from the group consisting of a glioma-associated antigen, carcinoembryonic antigen (CEA), β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyi esterase, mut hsp70-2, M-CSF, prostase, prostate-specific antigen (PSA), PAP, NY-ESO-1, LAGE-la, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin, EphA2, HER2, GD2, Glypican-3, 5T4, 8H9, αvβ6 integrin, BCMA, B7-H3, B7-H6, CAIX, CA9, CD19, CD20, CD22, kappa light chain, CD30, CD33, CD38, CD44, CD44v6, CD44v7/8, CD70, CD123, CD138, CD171, CEA, CSPG4, EGFR, EGFRvIII, EGP2, EGP40, EPCAM, ERBB3, ERBB4, ErbB3/4, FAP, FAR, FBP, fetal AchR, Folate Receptor a, GD2, GD3, HLA-AI MAGE Al, HLA-A2, IL1 1Ra, IL13Ra2, KDR, Lambda, Lewis-Y, MCSP, Mesothelin, Mucl, Mucl6, NCAM, NKG2D ligands, NY-ESO-1, PRAME, PSCA, PSC1, PSMA, ROR1, SURVIVIN, TAG72, TEM1, TEM8, VEGRR2, carcinoembryonic antigen, HMW-MAA, and VEGF receptors In other aspects, the invention provides for recombinant vectors encoding a cytokine to a tumor expressed cytokine receptor and a therapeutic agent as a fusion protein. In some embodiments, the cytokine receptor is a type I receptor or a type II receptor.

In other aspects, the invention provides for recombinant tumor cells comprising a vector as described above and herein. In some embodiments, the tumor cell expresses one or more fusion proteins.

In other aspects, the invention provides for methods of producing a recombinant tumor cell capable of expressing a fusion protein comprising an antibody or antibody fragment to a tumor-associated antigens (TAA) or tumor-specific antigens (TSA) and a therapeutic agent, said method comprising (a) introducing a vector as described above and herein into a tumor cell; and (b) culturing the tumor cell such that the vector is transduced into the tumor cell. In some embodiments, the vector and/or its components integrate in the tumor cells' genome. In some embodiments, the TAA or TSA is selected from the group consisting of glioma-associated antigen, carcinoembryonic antigen (CEA), β-human chorionic gonadotropin, alphafetoprotein (AFP), lectin-reactive AFP, thyroglubilin, RAGE-1, MN-CA IX, human telomerase reverse transcriptase, RU1, RU2 (AS), intestinal carboxyiesterase, mut hsp70-2, M-CSF, prostase, prostate-specific antigen (PSA), PAP, NY-ESO-1, LAGE-la, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin, EphA2, HER2, GD2, Glypican-3, 5T4, 8H9, αvβ6 integrin, BCMA, B7-H3, B7-H6, CAIX, CA9, CD19, CD20, CD22, kappa light chain, CD30, CD33, CD38, CD44, CD44v6, CD44v7/8, CD70, CD123, CD138, CD171, CEA, CSPG4, EGFR, EGFRvIII, EGP2, EGP40, EPCAM, ERBB3, ERBB4, ErbB3/4, FAP, FAR, FBP, fetal AchR, Folate Receptor a, GD2, GD3, HLA-AI MAGE Al, HLA-A2, IL1 1Ra, IL13Ra2, KDR, Lambda, Lewis-Y, MCSP, Mesothelin, Mucl, Mucl6, NCAM, NKG2D ligands, NY-ESO-1, PRAIVIE, PSCA, PSC1, PSMA, ROR1, SURVIVIN, TAG72, TEM1, TEM8, VEGRR2, carcinoembryonic antigen, HMW-MAA, and VEGF receptors. In some embodiments, the TAA or TSA is an antigen for a chimeric antigen receptor (CAR). In some embodiments, the TAA or TSA is an antigen for a T cell receptor (TCR). In some embodiments, the therapeutic agent is an antigen for an ADC antibody, ADCC antibody, and/or a radiotherapeutic antibody. In some embodiments, the therapeutic agent is an immunostimulatory cytokine or molecule selected from the group consisting of TLR agonists, PAMP, DAMP and other stimulators. In some embodiments, the therapeutic agent is a peptide with immunomodulatory or anti-tumor properties.

In other aspects, the invention provides for methods of treating cancer in an individual in need thereof comprising administering a composition comprising a vector as described above and herein. In some embodiments, a fusion protein is expressed. In other embodiments, the cancer cell expresses a therapeutic agent that increases immune response against the cancer cell. In some embodiments, the cancer cell express one or more protein or peptide antigens that is capable of being recognized by a CAR. In some embodiments, the cancer cell express one or more protein or peptide antigens that is capable of being recognized by a TCR. In some embodiments, the cancer cell express one or more fusion proteins containing therapeutic agents capable of being recognized by immune cells in the individual. In some embodiments, the method further comprises administration of CAR T cells to the individual.

DETAILED DESCRIPTION OF THE INVENTION

Figure 1:
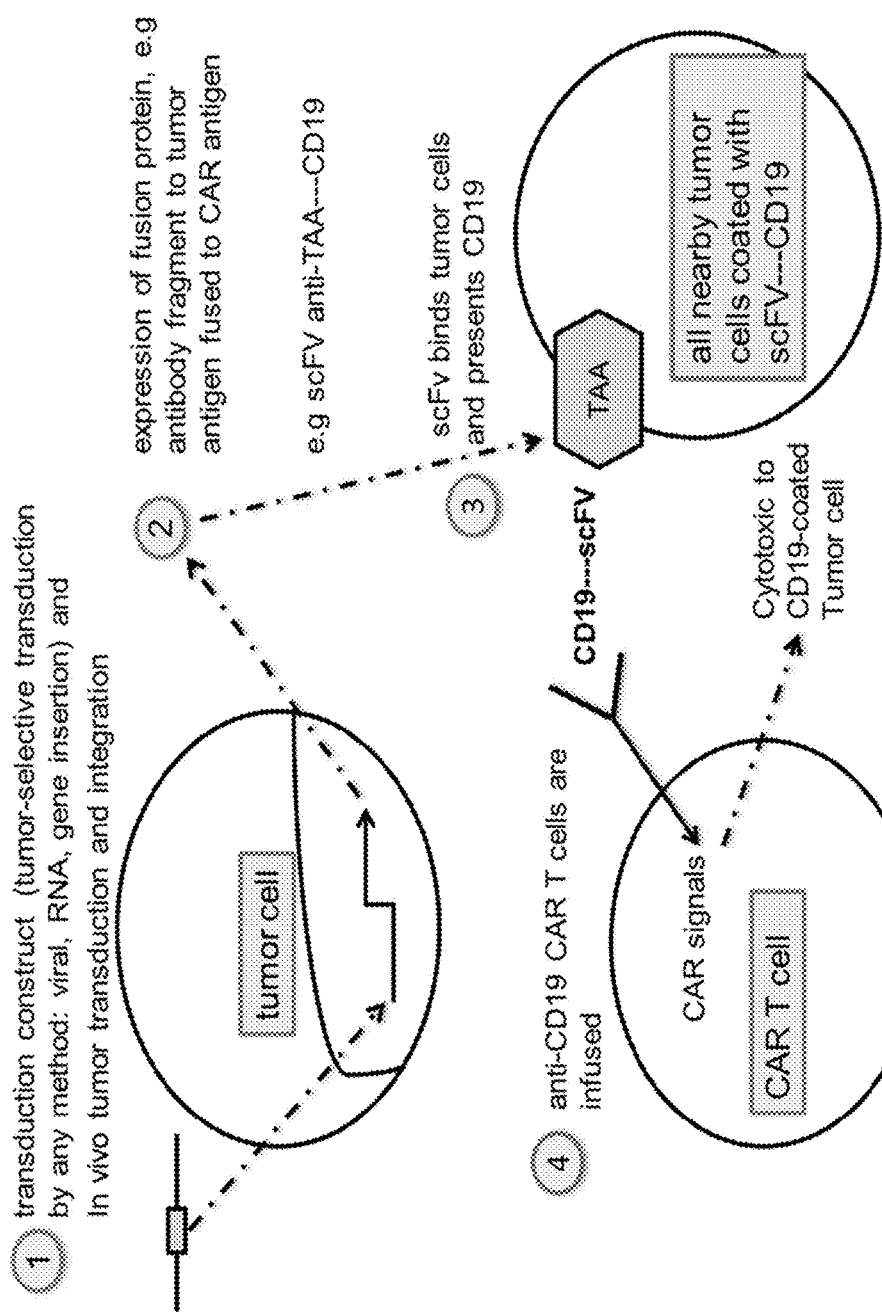
FIG. 1 is a schematic showing a non-limiting example of the methods of introduction of a cellular therapy target into solid tumor cells. Step one corresponds to the transduction construct (e.g., tumor-selective transduction via e.g., viral transduction, RNA transduction, and gene insertion), and/or in vivo transduction and integration. Step two corresponds to the expression of a fusion protein (e.g., an antibody fragment to a tumor antigen fused to a CAR antigen, for example an scFv anti-tumor associated antigen (TAA) fused to CD19 or a fragment thereof). Step three corresponds to the antibody fragment fused to an antigen, e.g. CD19, which binds to tumor cells and presents the antigen, and all nearby tumor cells are coated with the antibody fragment fused to a protein, peptide, or other agent, for example, CD19, which is an antigen recognized by CAR T cells. Step four corresponds to the infusion in vivo of CAR T cells that recognize the CAR antigen (e.g., anti-CD19 CAR T cells). The response becomes cytotoxic to the CD19-coated tumor cell.

The present invention is based, at least in part, upon the introduction of cellular therapy targets into solid tumor cells. Tumor cells can be transduced with fusion proteins such that the fusion proteins are secreted by the tumor cells and released to the tumor microenvironment to combat the tumor.

I. Definitions

As used herein, the term "antibody" refers to a polypeptide that includes canonical immunoglobulin sequence elements sufficient to confer specific binding to a particular target antigen. As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: CHL CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Intact antibody tetramers are composed of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. The Fc region of naturally-occurring antibodies binds to elements of the complement system, and also to receptors on effector cells, including for example effector cells that mediate cytotoxicity. As is known in the art, affinity and/or other binding attributes of Fc regions for Fc receptors can be modulated through glycosylation or other modification. In some embodiments, antibodies produced and/or utilized in accordance with the present disclosure include glycosylated Fc domains, including Fc domains with modified or engineered such glycosylation. For purposes of the present disclosure, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is polyclonal; in some embodiments, an antibody is monoclonal. In some embodiments, an antibody has constant region sequences that are characteristic of mouse, rabbit, primate, or human antibodies. In some embodiments, antibody sequence elements are fully human, or are humanized, primatized, chimeric, etc, as is known in the art. Moreover, the term "antibody" as used herein, can refer in appropriate embodiments (unless otherwise stated or clear from context) to any of the art-known or developed constructs or formats for utilizing antibody structural and functional features in alternative presentation. For example, in some embodiments, an antibody utilized in accordance with the present disclosure is in a format selected from, but not limited to, intact IgG, IgE and IgM, bi- or multi-specific antibodies (e.g., Zybodies®, etc), single chain Fvs, polypeptide-Fc fusions, Fabs, cameloid antibodies, masked antibodies (e.g., Probodies®), Small Modular ImmunoPharmaceuticals ("SMIPs™"), single chain or Tandem diabodies (TandAb®), VHHs, Anticalins®, Nanobodies®, minibodies, BiTE®s, ankyrin repeat proteins or DARPINs®, Avimers®, a DART, a TCR-like antibody, Adnectins®, Affilins®, Trans-bodies®, Affibodies®, a TrimerX®, MicroProteins, Fynomers®, Centyrins®, and a KALBITOR®. In some embodiments, an antibody may lack a covalent modification (e.g., attachment of a glycan) that it would have if produced naturally. In some embodiments, an antibody may contain a covalent modification (e.g., attachment of a glycan, a payload (e.g., a detectable moiety, a therapeutic moiety, a catalytic moiety, etc.), or other pendant group (e.g., poly-ethylene glycol, etc.)).

As used herein, an "antibody fragment" includes a portion of an intact antibody, such as, for example, the antigen-binding or variable region of an antibody. Examples of antibody fragments include Fab, Fab', F(ab')2, and Fv fragments; triabodies; tetrabodies; linear antibodies; single-chain antibody molecules; and multi-specific antibodies formed from antibody fragments. For example, antibody fragments include isolated fragments, "Fv" fragments (consisting of the variable regions of the heavy and light chains), recombinant single chain polypeptide molecules in which light and heavy chain variable regions are connected by a peptide linker ("ScFv proteins"), and minimal recognition units consisting of the amino acid residues that mimic the hypervariable region. In many embodiments, an antibody fragment contains sufficient sequence of the parent antibody of which it is a fragment that it binds to the same antigen as does the parent antibody; in some embodiments, a fragment binds to the antigen with a comparable affinity to that of the parent antibody and/or competes with the parent antibody for binding to the antigen. Examples of antigen binding fragments of an antibody include, but are not limited to, Fab fragment, Fab' fragment, F(ab')2 fragment, scFv fragment, Fv fragment, dsFv diabody, dAb fragment, Fd' fragment, Fd fragment, and an isolated complementarity determining region (CDR) region. An antigen binding fragment of an antibody may be produced by any means. For example, an antigen binding fragment of an antibody may be enzymatically or chemically produced by fragmentation of an intact antibody and/or it may be recombinantly produced from a gene encoding the partial antibody sequence. Alternatively or additionally, antigen binding fragment of an antibody may be wholly or partially synthetically produced. An antigen binding fragment of an antibody may optionally comprise a single chain antibody fragment. Alternatively or additionally, an antigen binding fragment of an antibody may comprise multiple chains which are linked together, for example, by disulfide linkages. An antigen binding fragment of an antibody may optionally comprise a multimolecular complex. A functional antibody fragment typically comprises at least about 50 amino acids and more typically comprises at least about 200 amino acids.

By "antigen" is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. Moreover, a skilled artisan will understand that an antigen need not be encoded by a "gene" at all. An antigen can be generated synthesized or can be derived from a biological sample. Such a biological sample can include, but is not limited to a tissue sample, a tumor sample, a cell or a biological fluid.

The term, "autologous" refers to any material derived from the same individual to which it is later re-introduced into the individual.

The term "cell therapy antigen" as used herein is meant to refer to one or more antigens (that are genetically engineered or naturally occurring) that can be recognized by effector cells (e.g., genetically engineered CAR T cell or genetically engineered or naturally occurring TCR). An antigen that is expressed on tumors (i.e., "tumor-associated antigen" or TAA) is one type of cell therapy antigen. An antigen that is expressed selectively on tumors (i.e., "tumor-selective antigen" or TSA) is also a type of cell therapy antigen. An antigen can also be expressed on tumor cells through therapeutic intervention, for example, by transducing tumor cells, in vivo, with genetic materials of the present invention, as described herein.

As used herein, the term "fusion protein" generally refers to a polypeptide including at least two segments, each of which shows a high degree of amino acid identity to a peptide moiety that (1) occurs in nature, and/or (2) represents a functional domain of a polypeptide. Typically, a polypeptide containing at least two such segments is considered to be a fusion protein if the two segments are moieties that (1) are not included in nature in the same peptide, and/or (2) have not previously been linked to one another in a single polypeptide, and/or (3) have been linked to one another through action of the hand of man.

The term "promoter" refers to a region of a DNA sequence that directs expression of genes. The promoter is typically upstream from the start of transcription start site and is involved in recognition and binding of RNA polymerase and other transcription machinery (e.g., other proteins) to initiate transcription of a polynucleotide sequence.

The term "solid tumor" is meant as an abnormal mass that usually does not contain cysts or liquid areas. Solid tumors can be benign or malignant. Different types of solid tumors are named for the types of cells that form them (such as sarcomas, carcinomas, and lymphomas). Examples of solid tumors such as sarcomas and carcinoma, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases.

An "individual" or "subject" can be a vertebrate, a mammal, or a human. Mammals include, but are not limited to, farm animals, sport animals, pets, primates, mice and rats. In one aspect, a subject is a human. An "individual" or "subject" can be a "patient" (e.g., under the care of a physician) but in some cases, an individual or subject is not a patient.

"Pseudoviruses" or "papilloma pseudoviruses" or "papillomavirus gene transfer vectors" refer to one or more papillomavirus capsid proteins that assemble and package heterologous nucleic acids (e.g., DNA) with or without viral nucleic acids (e.g., DNA) into infectious particles. The methods used to produce papilloma pseudoviruses are known in the art and are described, for example, in U.S. Pat. Nos. 6,599,739, 7,205,126, and 6,416,945; and in Buck and Thomspon, Production of Papillomavirus-Based Gene Transfer Vectors. Current Protocols in Cell Biology 26.1.1-26.1.19, Dec. 2007, all of which are incorporated by reference.

The term "T cell receptor" or "TCR" refers to a heterodimeric receptor found on the surface of T lymphocytes. TCRs are antigen-specific molecules that are responsible for recognizing antigenic peptides of the major histocompatibility complex (MHC) on the surface of antigen presenting cells (APCs), or any other nucleated cell. They are members of the immunoglobulin superfamily, and typically consist of two chains; alpha ($\alpha$) and beta ($\beta$), while a small subset of TCRs are formed by variable gamma ($\gamma$) and delta ($\delta$) chains. The chains pair on the surface of a T cell to form a heterodimeric receptor.

The term "transfected" or "transformed" or "transduced" is defined as a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny. In some embodiments, the host cell is a cancer cell, for example a tumor cell such as solid tumor cell.

The term "tropism" refers to the movement or targeting of a viral vector towards a receptor.

A "vector" is a composition which comprises an isolated nucleic acid, and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus and phage vectors (AAVP), retroviral vectors, human papilloma virus (HPV) pseudovirus vectors, and the like.

II. Compositions

The invention provides for compositions that can be used for introduction of fusion proteins into cancer cells (e.g., tumor cells) that will make the cancer cells more susceptible for destruction by either an individual's immune system and/or additional therapeutic agents. Compositions can include, but are not limited to, vectors and various constructs described herein, host cells (including tumor cells) containing such vectors and/or constructs, host cells expressing or capable of expressing these vectors and/or constructs, kits containing the vectors, constructs, instructions, and/or reagents and the like.

Cancer cells (e.g., tumors) can be transduced with fusion proteins. As the fusion proteins are expressed (and/or secreted), the proteins can also permeate the tumor microenvironment. Non-limiting examples of fusion proteins contemplated by the invention include: antibody fusions so that the antibody or antibody fragment that bind to one or more tumor-associated antigens (TAA) or tumor-specific antigens (TSA), cytokine target fusions, bi-specific T-cell engagers (BITES) or CD19 variants.

Vector Design

The nucleic acid sequences coding the desired gene of interest can be cloned into a number of types of vectors. For example, the nucleic acid can be cloned into a plasmid, a phagemid, a phage derivative, an animal virus, and a cosmid. Other vectors can include expression vectors, replication vectors, probe generation vectors, sequencing vectors, and viral vectors. In other examples, the vector can be a foamy viral (FV) vector, a type of retroviral vector made from spumavirus. Viral vector design and technology is well known in the art as described in Sambrook et al, (Molecular Cloning: A Laboratory Manual, 2001), and in other virology and molecular biology manuals.

Transduction Methods

Transfer of nucleic acid to a cell for gene-modification of the cell in order for the cell to express a gene of interest is widely performed via transduction (e.g., viral transduction). The nucleic acid sequence coding for the desired gene of interest or portion thereof (e.g., tumor associated antigen) can be obtained using recombinant methods known in the art. Exemplary methods include screening libraries from cells expressing the gene, deriving the gene from a vector, or isolating directly from cells and tissues. These methods are performed using standard techniques. In other embodiments, the gene of interest can be produced synthetically rather than cloned. Gene delivery methods are well-known in the art, for example, U.S. Pat. No. 5,399,346.

Viral transduction

Viruses are highly efficient at nucleic acid delivery to specific cell types, while often avoiding detection by the infected host immune system. These features make certain viruses attractive candidates as vehicles for introduction of cellular therapy targets into cancer cells, e.g., solid tumor cells. A number of viral based systems have been developed for gene transfer into mammalian cells. Examples of viral vectors include, but are not limited to, retroviruses, adenoviruses, adeno-associated viruses, herpes viruses, lentiviruses, poxviruses, herpes simplex 1 virus, herpes virus, oncoviruses (e.g., murine leukemia viruses), and the like. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

Lentiviral and Retroviral transduction can be enhanced by the addition of polybrene (SantaCruz sc-134220; Millipore TR-1003-G; Sigma 107689), a cationic polymer (also known as hexamehtrine bromide) that is used to increase the efficiency of the retrovirus transduction.

For example, retroviruses provide a platform for gene delivery systems. Retroviruses are enveloped viruses that belong to the viral family Retroviridae. Once in a host's cell, the virus replicates by using a viral reverse transcriptase enzyme to transcribe its RNA into DNA. The retroviral DNA replicates as part of the host genome, and is referred to as a provirus. A selected gene can be inserted into a vector and packaged in retroviral particles using techniques known in the art. The recombinant virus can then be isolated and delivered to cells of the subject either in vivo or ex vivo. A number of retroviral systems are known in the art, for example See U.S. Pat Nos. 5,994,136, 6,165, 782, and 6,428,953.

Retroviruses include the genus of *Alpharetrovirus* (e.g., avian leukosis virus), the genus of *Betaretrovirus*; (e.g., mouse mammary tumor virus) the genus of *Deltaretrovirus* (e.g., bovine leukemia virus and human T-lymphotropic virus), the genus of *Epsilonretrovirus* (e.g., Walleye dermal sarcoma virus), and the genus of *Lentivirus*.

In other embodiments, the retrovirus is a lentivirus a genus of viruses of the Retroviridae family, characterized by a long incubation period. Lentiviruses are unique among the retroviruses in being able to infect non-dividing cells; they can deliver a significant amount of genetic information into the DNA of the host cell, so they are one of the most efficient methods of a gene delivery vector. Lentiviral vectors have an advantage to other viral vectors in that they can transduce non-proliferating cells and show low immunogenicity. In some examples, the lentivirus includes, but is not limited to human immunodeficiency viruses (HIV-1 and HIV-2), simian immunodeficiency virus (S1V), feline immunodeficiency virus (FIV), equine infections anemia (EIA), and visna virus. Vectors derived from lentiviruses offer the means to achieve significant levels of gene transfer in vivo.

In embodiments, the vector is an adenovirus vector. Adenoviruses are a large family of viruses containing double stranded DNA. They replicate the DNA of the host cell, while using the host's cell machinery to synthesize viral RNA DNA and proteins. Adenoviruses are known in the art to affect both replicating and non-replicating cells, to accommodate large transgenes, and to code for proteins without integrating into the host cell genome.

In some embodiments, an AAVP vector is used. The AAVP vector is a hybrid of prokaryotic-eukaryotic vectors, which are chimeras of genetic cis-elements of recombinant adeno-associated virus and phage. An AAVP combines selected elements of both phage and AAV vector systems, providing a vector that is simple to produce in bacteria with no packaging limit, while allowing infection of mammalian cells combined with integration into the host chromosome. Vectors containing many of the appropriate elements are commercially available, and can be further modified by standard methodologies to include the necessary sequences. Among other things, AAVPs do not require helper viruses or trans-acting factors. In addition, the native tropism of AAV for mammalian cells is eliminated since there is not AAV capsid formation. Other methods and details are in U.S. Pat. No. 8,470,528 and Hajitou A. et al., Cell, 125: 358-398, both of which are incorporated herein by reference.

In other aspects, a human papilloma (HPV) pseudovirus is used. Recent studies have shown that DNA plasmids can be packaged into papillomavirus L1 and L2 capsid protein to generate pseudovirion that can efficiently deliver DNA. The encapsulation protects the DNA from nucleases and provides a targeted delivery with great stability. Many of the safety concerns associated with the use of viral vectors are mitigated with the HPV pseudoviros because its construct is different from the natural HPV viral genome. Other methods and examples are in Hung, C., et al., *Plos One*, 7:7 (e40983); 2012, U.S. Pat. No. 8,394,411, and Kines, R., et al *Int J of Cancer*, 2015, all of which are incorporated herein by reference.

In some aspects, an oncolytic virus is used. Oncolytic virus therapy selectively replicates the virus in cancer cells, and subsequently spreads within a tumor without affecting normal tissue. Alternatively, the oncolytic virus preferentially infects and kills cells without causing damage to normal tissues. Oncolytic viruses are also effective at inducing immune responses to themselves as well as to the infected tumor cell. Typically, oncolytic viruses fall into two classes: (I) viruses that naturally replicate preferentially in cancer cells and are nonpathogenic in humans. Exemplary class (I) oncolytic viruses include autonomous parvoviruses, myxoma virus (poxvirus), Newcastle disease virus (NDV; paramyxovirus), reovirus, and Seneca valley virus (picornavirus). A second class (II), include viruses that are genetically manipulated for use as vaccine vectors, including measles virus (paramyxovirus), poliovirus (picornavirus), and vaccinia virus (poxvirus). Additionally, oncolytic viruses may include those genetically engineered with mutations/deletions in genes required for replication in normal but not in cancer cells including adenovirus, herpes simplex virus, and vesicular stomatitis virus. Oncolytic viruses can be used as a viral transduction method due to their low probability of genetic resistance because they can target multiple pathways and replicate in a tumor-selective method. The viral dose within the tumor can increase with time due to in situ viral amplification (as compared to small molecule therapies which decrease with time), and safety features can be built in (i.e., drug and immune sensitivity).

Integration

In some aspects of the invention, the nucleic acids encoding cellular therapy target(s) or tumor-associated antigen(s) are integrated as part of the tumor cells' genetic makeup. Without being bound by theory, integration of the nucleic acid encoding cellular therapy target(s) can be helpful in that as the tumor cell replicates, progeny tumor cells would express the cellular therapy target(s) and, as such, be susceptible to the effector cells and other therapeutic agents (including combination therapy agents). It follows that in some indications, such as metastatic disease, the state of rapid tumor cell proliferation becomes useful in propagating the therapeutics of the present invention.

In one embodiment, integration can be achieved by using viruses that naturally integrate into the host cell. Integration is a crucial step in replication of retroviruses as it is a virus genome that has been integrated into the DNA of a host cell. Integration is not part of the viral replication cycle, but it can occasionally occur. The virus does not directly make new DNA copies of itself while integrated into the host genome; alternatively, it is passively replicated along with the host genome and passed on to the original cell's offspring. Integration of the viral DNA results in permanent insertion of the viral genome into the host chromosomal DNA, referred as a provirus in the case of retroviruses.

In other embodiments, integration can be achieved by commercially available kits, including the CompoZr® Targeted Integration Kit which is designed to integrate a gene of interest into the adeno-associated virus integration site 1 (AAVS1) on human chromosome 19.

In addition to the expression of TAA, the cancer cells (e.g., solid tumor cells) can be engineered so that they also express one or more fusion protein of an antibody or antibody fragment (e.g., scFv) coupled to an antigen that an effector cell will recognize. The antibody or antibody fragment recognizes the tumor cell and binds and presents the antigen for an effector cell to recognize. In one non-limiting example, a solid tumor cell can be transduced with a fusion protein that includes an anti-tumor TAA scFv that binds to a tumor cell, and also part or all of the human CD19 protein. The scFv portion binds to the tumor cell and the CD19 is presented to effector cells for them to target the tumor cell and destroy the tumor cell. The effector cells can be naturally occurring or genetically engineered.

Expressed Gene Approach for Solid Tumor Targeting

Genes productively introduced into tumor cells will provide improved cellular therapeutic activity by addressing or circumventing critical barriers to efficacy. These genes will improve therapeutic efficacy by "propagating" the anti-tumor response, optimize cytokine support in the local environment, reverse local immunosuppression, improve cellular effector functions, and promote cellular access to tumors. Any gene can be included in an expressed construct as described herein, and the present disclosure is not limited to any particular gene. Exemplary, non-limiting types of genes that can be included as cellular therapy targets include, e.g., targets for additional cellular therapeutics, polypeptide antigens, antibodies, cytokines, agents targeting tumor microenvironment, and agents supporting immune cell growth/proliferation.

An expressed gene contains a promotor with its associated elements, and a gene sequence. An expressed gene contains three essential characteristics: 1) an optimal promoter for expression in the tumor cell, 2) an optimal expressed gene sequence, and 3) an optimized expression pattern with defined kinetics.

A set of promoters is developed to drive diverse expression patterns. Examples include; rapid and sustained expression, measured in days, or rapid but reversible expression, or delayed expression. Also, the level of expression can be modified by selective use of regulatory and promoter elements. Such methods are well understood, for example, E. D. Papadakis, et al., *Current Gene Therapy*, 4: 89-113 (incorporated herein by reference).

III. Methods for Treating Cancer

The invention provides for compositions and methods for treating cancer by engineering a system whereby the cancer cells (e.g., tumor cells or solid tumor cells) secrete fusion proteins that include TAA or TSA and a therapeutic agent. An individual having cancer or suspected of having cancer can be given a composition that allows for the in vivo transduction of their cancer cells. The administration can be by any means, including, but not limited to intravenously, systemically, intramuscularly, intraperitonally, or intra-tumoral injection.

Targets for Additional Cellular Therapeutics

In some embodiments, the cell therapy antigen that is expressed on local tumor cells following transduction and secretion of fusion proteins is recognized by the effector cells, and can comprise a tumor associated antigen (TAA). In one embodiment, TAA expression can be restricted to the tumor cell population alone, expressed by all tumor cells, and expressed on the tumor cell surface. Other antigens are overexpressed on tumor cells, but may be found on normal cells at lower levels of expression and thus are tumor-selective antigens (TSA). In addition, some tumor antigens arise as "passenger mutations", i.e. are non-essential antigens expressed by tumor cells that have defective control over DNA repair, thus accumulating mutations in diverse proteins. Some tumor antigens are proteins that are produced by tumor cells that elicit an immune response; particularly T-cell mediated immune responses. Tumor-specific molecules that may be targeted by cellular therapy targets may include tumor associated antigens well known in the art and can include, for example, a glioma-associated antigen, carcinoembryonic antigen (CEA), β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-la, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin. The application of technologies, including next generation sequencing (NGS) of tumor genomes and exomes, and high-sensitivity mass spectrometry (protein sequencing) analysis of the tumor proteome, is continuing to identify novel TAA and TSA antigens of use for this invention.

NGS is a method of high-throughput sequencing that performs massively parallel sequencing, during which millions of fragments of DNA from a single sample are sequenced in unison. NGS facilitates high-throughput sequencing, which allows an entire genome to be sequenced in less than one day. The creation of NGS platforms has made sequencing accessible to more labs, rapidly increasing the amount of research and clinical diagnostics being performed with nucleic acid sequencing, and thus have revolutionized genomics and molecular biology. Some NGS technologies include Illumina (Solexa) sequencing, Roche 454 sequencing, Ion torrent: proton/PGM sequencing, and SOLiD sequencing.

An alternative method for identifying tumor specific antigens is direct protein sequencing. Protein sequencing of enzymatic digests using multidimensional MS techniques (MSn) including tandem mass spectrometry (MS/MS)) can also be used to identify antigens. Such proteomic approaches permit rapid, highly automated analysis (See, e.g., K. Gevaert and J. Vandekerckhove, *Electrophoresis* 21: 1145-1154 (2000, incorporated herein by reference)). Furthermore, high-throughput methods for de novo sequencing of unknown proteins may be used to analyze the proteome of a patient's tumor to identify expressed antigens. For example, meta shotgun protein sequencing may be used to identify expressed antigens (See e.g., Guthals et al. (2012), *Molecular and Cellular Proteomics* 11(10): 1084-96, incorporated herein by reference).

Non-limiting examples of tumor antigens that can used include EphA2, HER2, GD2, Glypican-3, 5T4, 8H9, αvβ6 integrin, BCMA, B7-H3, B7-H6, CAIX, CA9, CD19, CD20, CD22, kappa light chain, CD30, CD33, CD38, CD44, CD44v6, CD44v7/8, CD70, CD123, CD138, CD171, CEA, CSPG4, EGFR, EGFRvIII, EGP2, EGP40, EPCAM, ERBB3, ERBB4, ErbB3/4, FAP, FAR, FBP, fetal AchR, Folate Receptor a, GD2, GD3, HLA-AI MAGE Al, HLA-A2, IL1 1Ra, IL13Ra2, KDR, Lambda, Lewis-Y, MCSP, Mesothelin, Mucl, Mucl6, NCAM, NKG2D ligands, NY-ESO-1, PRAME, PSCA, PSC1, PSMA, ROR1, SURVIVIN, TAG72, TEM1, TEM8, VEGRR2, carcinoembryonic antigen, HMW-MAA, and VEGF receptors. Other exemplary antigens that can be used are antigens that are present within in the extracellular matrix of tumors, such as oncofetal variants of fibronectin, tenascin, or necrotic regions of tumors.

Additional tumor-selective molecules can be used include any membrane protein or biomarker that is expressed or overexpressed in tumor cells including, but not limited to, integrins (e.g., integrin αvβ3, α5β1), EGF Receptor Family (e.g., EGFR2, Erbb2/HER2/neu, Erbb3, Erbb4), proteoglycans (e.g., heparan sulfate proteoglycans), disialogangliosides (e.g., GD2, GD3), B7-H3 (aka CD276), cancer antigen 125 (CA-125), epithelial cell adhesion molecule (EpCAM), vascular endothelial growth factor receptors 1 and 2 (VEGFR-1, VEGFR-2), CD52, carcinoembryonic antigen (CEA), tumor associated glycoproteins (e.g., TAG-72), cluster of differentiation 19 (CD19), CD20, CD22, CD30, CD33, CD40, CD44, CD74, CD152, mucin 1 (MUC1), tumor necrosis factor receptors (e.g., TRAIL-R2), insulin-like growth factor receptors, folate receptor a, transmembrane glycoprotein NMB (GPNMB), C-C chemokine receptors (e.g., CCR4), prostate specific membrane antigen (PSMA), recepteur d'origine nantais (RON) receptor, cytotoxic T-lymphocyte antigen 4 (CTLA4), and other tumor specific receptors or antigens.

As exemplified by the non-limiting examples of TAA and TSA targets recited herein, there is a large and diverse selection of antigens to which one of skill in the art can direct the transduced and expressed therapeutics described herein. For example, the therapeutics might comprise a secreted fusion protein that contains a scFv antigen binding domain (e.g. anti-MUC16, anti-CEA, anti-PSMA) fused to the target antigen (e.g. CD19) that can be recognized by a CAR T cell. In this embodiment, the secreted fusion protein has two functional domains, the scFv that binds to the target tumor cell surface, and the CD19 protein domain that is presented as a target for the CAR T cell (FIG. 1). It will be immediately apparent that the scFv can be selected to target one of many diverse antigens, and that the protein domain to be recognized by the cellular therapeutic (also, the "effector cell" of the present invention), can also be diverse, e.g. recognized by a specific CAR T cell, or a TCR T cell, or a characterized TIL or an NK cell. It will be further recognized that modern antibody engineering allows the use of bispecific recognition to be built into the scFv portion of the therapeutic, such that effective binding to the tumor cells is accomplished only when both arms of a bispecific scFV can bind. The range of bispecific technologies available is broad and the molecular biology and protein chemistry tools and principles required for effective bispecific antibody engineering are well understood, see for example, Kontermann, R. *MAbs* 2012; 4(2) 182-97 (incorporated herein by reference).

Further, multiple genes can be encoded in a single CAR expression construct by using, for example, in frame or independent IRES initiation sites for individual elements. Alternatively, inducible methods have been described, whereby the application of a small molecule can induce or block expression of one or more CAR elements. A wide variety of such methods are disclosed, such as inhibitory CARs, costimulatory CARs, "cideCARs", on switches and others, the use of which can further modify or alter the activity of CAR T cells (see Baas, T. SciBX 7(25); doi: 10.1038/scibx.2014.725).

Antibody-drug Conjugate Targets

In other embodiments, the transduced tumor cells secrete fusion proteins that are targeted by antibody-drug conjugates that are known and include, e.g., brentuximab vedotin (ADCETRIS, Seattle Genetics); trastuzumab emtansine (Roche); Gemtuzumab ozogamicin (Pfizer); CMC-544; SAR3419; CDX-011; PSMA-ADC; BT-062; CD30, HER2, and IMGN901 (see, e.g., Sassoon et al., Methods Mol. Biol. 1045:1-27 (2013); Bouchard et al., Bioorganic Med. Chem. Lett. 24: 5357-5363 (2014)). In other embodiments, the transduced tumor cells secrete fusion protins which can be targeted by antibodies having antibody dependent cellular cytotoxicity function such as those recognized by rituximab, ocrelizumab, ipilimumab, cituximab, erbitux and many others. Accordingly, in some embodiments, a nucleic acid encoding a polypeptide antigen as part of the fusion protein that binds to one or more of such known antibody-drug conjugates can be included in as a cellular therapy target described herein.

Cytokine Fusion Proteins

In some embodiments, the tumor and tumor microenvironment is transduced with a cytokine fusion protein, e.g., a fusion protein of a cytokine (e.g., an anti-tumor cytokine) and a target for one or more additional cellular therapeutics described herein (e.g., a CAR-T target). Exemplary cytokines may bind to the tumors, and present the tumor with the cytokine. For example, some contemplated targets include CD19, CD20, CD21, CD22, CD24, and BCMA. Such a cellular therapy can provide both a target for one or more additional cellular therapeutics (e.g., a CAR-T target) and a stimulatory cytokine at a tumor surface. For example, an expressed and/or secreted construct can encode a cytokine-CD19 fusion protein, or a fusion of a cytokine and a CD19 fragment, e.g., a CD19 fragment to which a CD19-CAR-T cell binds. In some embodiments, a CD19 fragment is a CD19 IgC domain. Without wishing to be bound by theory, a single expressed construct encoding such a fusion protein advantageously allows a cellular therapeutic to be genetically engineered using a minimal (e.g., a single) transgene. An additional benefit of using cytokine fusion proteins is to utilize their tight binding to their receptors, in addition to the cytokine functional effect.

In some embodiments, one or more cytokines secreted as part of a cytokine fusion protein bind to cells at high affinity (e.g., KD of about $10^{-7}$, $10^{-8}$, $10^{-9}$, $10^{-10}$, $10^{-11}$, or less) and/or have low internalization rates (e.g., less than about 10, $10^2$, $10^3$, $10^4$, or $10^5$ cytokine molecules per cell per day). Binding affinity and internalization rates of various cytokines are known in the art and/or can be measured using known methods.

Pro-immune Response Agents

In some embodiments, the recombinant tumor described herein encodes, as a fusion protein as described herein, one or more pro-immune response agents, e.g., one or more cytokines used in cancer therapy. Non-limiting, exemplary cytokines that can be included include, e.g., IFNα, IFNβ, IFNγ, IL-1, IL-2, IL-7, IL-12, IL-15, IL-21, IL-36, TNF, LTα, GM-CSF, G-CSF, a TLR agonist, and an immune checkpoint antibody fragment.

Known problems associated with cytokine therapy include, e.g., high dose requirements, toxicity, and limited efficacy. Thus, in some embodiments, expressed constructs are used to deliver one or more cytokines at a specific site and/or at a specific dose (e.g., to reduce or eliminate one or more risks associated with cytokine therapy).

In some embodiments, expression of a cytokine (e.g., an immunostimulatory cytokine) at or near a surface of a tumor induces an immune response to the tumor. In some embodiments, an expressed cytokine fusion protein can be a target for one or more additional cellular therapeutics (e.g., one or more additional CAR-T cells). In some embodiments, secretion of a cytokine fusion protein near a surface of a tumor induces an immune response to the tumor and is also used as a target for one or more additional cellular therapeutics (e.g., one or more additional CAR-T cells). An example is an Interferon alpha cytokine fused to the CD19 protein domain recognized by a CAR T cell with CD19 reactivity. The IFNalpha molecule binds with high affinity to interferon receptors on or near the tumor cell, thus supporting cellular therapeutic activity directed to CD19. In another example, the interferon alpha cytokine is fused to a scFV that recognizes a TAA or a TSA on the same tumor cell type, thus binding back on to the cell and surrounding cells, and inducing or supporting an IFNalpha-driven immune response.

For example, release of IL-21 can be used to induce expansion and/or effector differentiation of CD8+ T cells and/or support NK cell activation and cytolytic activity. In one exemplary method, an expressed construct encodes IL-21. Upon binding of a scFv directed an antigen on a tumor cell, a cellular therapeutic described herein exhibits prolonged release of IL-21. Exemplary cellular therapeutics include, e.g., CAR-T cells, CAR-NK cells, TCR-T cells, TIL cells, allogenic NK cells, and autologous NK cells.

In another exemplary method, induced release of IL-15 fusion proteins can be used to support NK cell expansion and/or to recruit NK cells to promulgate an anti-tumor response and to support the survival and expansion of cellular therapeutics. Exemplary cellular therapeutics include, e.g., CAR-T cells, CAR-NK cells, TCR-T cells, TIL cells, allogenic NK cells, and autologous NK cells. In this example a scFv that recognizes a TAA or a TSA on the target tumor cell type binds, and presents IL-15 in the local environment. In a further exemplification, of relevance to all of the cytokine examples proposed, the secreted fusion protein is trifunctional, having a scFV that recognizes a TAA or a TSA on the target tumor cell type, a cytokine encoded into a beta loop or beta strand within the heavy or light chain variable region that is not engaged in antigen binding, and expressing a target antigen for the binding of a cellular therapeutic. The utilization of CDRs within the heavy and light variable domains of a scFv is readily determined from the sequence of the CDR as well as through the use of databases that indicate which residues are involved in antigen engagement and which are not involved but are otherwise solvent exposed, i.e. useful for expression of an encoded sequence such as a cytokine.

Cell Recruiting Moieties

In some examples, the recombinant tumor cells can express, as part of a fusion protein, scFv or TCR that may be fused to cell recruiting moieties (e.g., anti-CD3 or anti-CD16). In other embodiments, bispecific T cell engager (BiTE®) technology is utilized to help engage the body's endogenous T cells and to target cancer cells that have been engineered to express one or more TAA's. The antibody constructs of the BiTE® technology are constructed by genetically linking the minimal binding domains of monoclonal antibodies for TAA or tumor-associated surface antigens and for the T cell receptor-associated molecule, onto a single polypeptide chain. One antibody is specific for a selected surface antigen on a targeted tumor cell, and the other antibody is specific for moiety (e.g., CD3), tied to the T-cell receptor complex on the surface of T cells. The BiTE® technology binds polyclonal cytotoxic T cells and targeted malignant cells.

Polypeptide Antigens

In some embodiments, a target for one or more additional cellular therapeutics is or comprises a polypeptide antigen. The polypeptide antigen to be expressed by an expressed construct, and is not limited to any particular polypeptide or portion thereof, provided that an additional cellular therapeutic (e.g., CAR-T cell) can be engineered to recognize and bind to such polypeptide target. In some embodiments, the polypeptide target is a polypeptide that is not a tumor-associated antigen. In some embodiments, the target is a tumor antigen, e.g., BCMA, CD19, CD20, CD22, ROR1, mesothelin, CD33/IL3Ra, c-Met, PSMA, Glycolipid F77, EGFRvIII, GD-2, NY-ESO-1 TCR, or MAGE A3 TCR.

Antibody Fusion Proteins

In some embodiments, the tumor and tumor microenvironment is transduced with a fusion protein comprising an antibody (or antigen-binding fragment thereof, e.g., secreted scFv or other antibody formats) and a target for one or more additional cellular therapeutics (e.g., a CAR-T target). An antibody (or fragment) can be selected to bind, e.g., to a tumor antigen (e.g., a tumor antigen described herein), and its fusion partner can include a target for one or more additional cellular therapeutics. Such antibodies (or antigen-binding fragments) include, e.g., a monoclonal antibody (mAb), including, for example, scFv and full length mAbs, a VHH domain, a diabody, a nanobody, etc. In one example, a construct encodes a secreted fusion protein consisting of a mAb (e.g., an anti-tumor associated antigen mAb or antigen-binding fragment) and CD19 or a fragment thereof (e.g., a CD19 Ig domain).

In some embodiments, an antibody (or fragment) binds to an antigen expressed on several types of cells. In some embodiments, an antibody (or fragment) binds to a tumor-selective antigen. In some embodiments, an antibody (or fragment) binds to a tumor-selective, but not specific, antigen. In some embodiments, an antibody (or fragment) binds to a tumor antigen associated with a hematologic malignancy. In some embodiments, an antibody (or fragment) binds to a tumor antigen associated with a solid tumor. In some embodiments, an antibody (or fragment) binds to one or more of BCMA, CD19, CD20, CD22, ROR1, mesothelin, CD33/IL3Ra, c-Met, PSMA, Glycolipid F77, EGFRvIII, GD-2, NY-ESO-1 TCR, and MAGE A3 TCR.

The target, which is placed on the tumor cells, can be CD19. Other B cell targets can be used, including but not limited to CD20, CD21, CD22, CD23, CD24, CD72, CD79a, CD79b, and BCMA. These B cell targets have particular advantages as CAR T cell targets, along with the list of other targets. In addition, the target can include CD30, Her 2, a target for ADC's or radioimmunotherapy (e.g., a monoclonal antibody carrying a radioisotope).

Peptides that Inhibit Local (e.g., Tumor Microenvironment) Factors

In some embodiments, peptides (e.g., polypeptides and fragments thereof) that inhibit local factors can be expressed as a fusion protein by the tumor cell. Nucleic acids coding for these peptides can be engineered as described herein and/or by any method known to one of skill in the art such that the peptide(s) are expressed. Non-limiting examples include TGFbeta, adenosine receptor 2, vascular endothelial growth factor (VEGF), platelet-derived growth factor (PDGF), indoleamine 2,3-dioxygenase 1 (IDO1), and matrix metalloproteinases (MMPs)).

CD19 as a Scaffold for Inducible CD19 Variant Proteins and CD19 Variant Fusion Proteins CD19 is a 95 kd transmembrane glycoprotein belonging to the Ig superfamily and includes two extracellular C2-type Ig domains (see, e.g., Tedder Nature Rev. Rheum. 5:572-577 (2009); Wang et al., Exp. Hematol. Oncol. 2012 Nov 29; 1(1):36. doi: 10.1186/2162-3619-1-36. )). In some embodiments, one or both of the C2-type Ig domains are used as scaffolds for mutagenesis, and CD19 variants (e.g., CD19 or a portion thereof that include one or more mutations within one or both C2-type Ig domains) can be screened and selected for binding to a target antigen described herein.

The nucleotide sequence of human CD19 is known (see Genbank Accession No. M84371.1). To provide variant nucleic acid sequences that encode CD19 variants that bind a particular antigen, a number of methods known in the art may be utilized. In some embodiments, a screening procedure is used that enables identification and/or isolation of nucleic acids that encode CD19 variants that bind a particular antigen. Exemplary methods include a so-called biopanning step, known from technologies such as phage display (Kang, A. S. et al. 1991. Proc Natl Acad Sci USA 88, 4363-4366), ribosome display (Schaffitzel, C. et al. 1999. J. Immunol. Methods 231, 119-135), DNA display (Cull, M. G. et al. 1992. Proc Natl Acad Sci USA 89, 1865-1869), RNA-peptide display (Roberts, R. W., Szostak, J. W., 1997. Proc Natl Acad Sci USA 94, 12297-12302), covalent display (WO 98/37186), bacterial surface display (Fuchs, P. et al. 1991. Biotechnology 9, 1369-1372), yeast surface display (Boder, E. T., Wittrup, K. D., 1997. Nat Biotechnol 15, 553-557) and eukaryotic virus display (Grabherr, R., Ernst, W., 2001. Comb. Chem. High Throughput. Screen. 4, 185-192). FACS and magnetic bead sorting are also applicable for enrichment (panning) purposes using labeled antigen. Immunodetection assays such as ELISA (Dreher, M. L. et al. 1991. J. Immunol. Methods 139, 197-205) and ELISPOT (Czerkinsky, C. C. et. al. 1983. J Immunol Methods. 65, 109-21) can also be used either following a biopanning step or alone.

Thus, in some embodiments, an inducible construct described herein encodes a CD19 variant (or fragment), either alone or as part of a fusion protein described herein. For example, an inducible construct described herein can encode a CD19 variant (or fragment) selected to bind to a tumor agent and which, upon expression, can bind to the tumor antigen and that itself can be a target for an additional cellular therapeutic (e.g., a CAR-T cell that binds CD19). In some embodiments, an inducible construct described herein encodes a CD19 variant that includes a C2-type Ig domain variant selected to bind a tumor antigen. Upon expression of the CD19 variant, the C2-type Ig domain binds to the tumor antigen on a tumor cell. Subsequently, treatment with (e.g., administration to a subject of) a CAR-T cell that recognizes CD19 kills the tumor cell to which the CD19 variant is bound. In some embodiments, an inducible construct described herein encodes a CD19 variant that includes variants of both C2-type Ig domains, each of which is selected to bind a tumor antigen (e.g., different epitopes of the tumor antigen). Upon expression of the CD19 variant, the C2-type Ig domains bind to the tumor antigen on a tumor cell. Subsequently, treatment with (e.g., administration to a subject of) a CAR-T cell that recognizes CD19 kills the tumor cell to which the CD19 variant is bound.

In some embodiments, a CD19 variant selected for binding to a target antigen is included in a fusion protein. For example, a CD19 variant that includes a C2-type Ig domain variant selected to bind a tumor antigen can be fused to an antibody or fragment thereof that also binds to the tumor antigen (e.g., to a different epitope on the tumor antigen). Exemplary fusion proteins include, e.g., CD19 variant/scFv fusion proteins and CD19 variant/VHH fusion proteins. An inducible construct described herein can encode such a CD19 variant/antibody fusion protein and upon expression, the CD19 variant and the antibody of the fusion protein bind to the tumor antigen on a tumor cell. Subsequently, treatment with (e.g., administration to a subject of) a CAR-T cell that recognizes CD19 kills the tumor cell to which the CD19 variant/antibody fusion protein is bound. In some embodiments, as described herein, the CD19 scaffold genes that are useful in the context of inducible expression will also be useful when modified for the production in vitro of soluble, purified fusion proteins. Additional, non-limiting examples of fusion proteins that include CD19 variants (or fragment) as a scaffold include, e.g., CD19 variant/cytokine fusion proteins and CD19 variant/TLR agonist fusion proteins.

Additional, non-limiting examples of fusion proteins that include CD19 (or fragment) as a scaffold include, e.g., CD19-cytokine fusion proteins, CD19-TLR agonist fusion proteins. Other B cell restricted cell surface markers which contain immunoglobulin-like domains include CD22, CD79a and CD79b. These Ig domains can also be mutagenized to generate variants binding TAA's and TSA's.

Polypeptide Antigens and Antibodies

The below Table 1 presents a non-comprehensive list of certain human polypeptide antigens targeted by known, available antibody agents, and notes certain cancer indications for which the antibody agents have been proposed to be useful:

TABLE 1

| Human Antigen | Antibody (commercial or scientific name) | Cancer indication |
| --- | --- | --- |
| CD2 | Siplizumab | Non-Hodgkin's Lymphoma |
| CD3 | UCHT1 | Peripheral or Cutaneous T-cell Lymphoma |
| CD4 | HuMax-CD4 | |
| CD19 | SAR3419, MEDI-551 | Diffuse Large B-cell Lymphoma |
| CD19 and CD3 or CD22 | Bispecific antibodies such as Blinatumomab, DT2219ARL | Non-Hodgkin's Lymphoma |
| CD20 | Rituximab, Veltuzumab, Tositumomab, Ofatumumab, Ibritumomab, Obinutuzumab, | B cell malignancies (Non-Hodgkin's lymphoma, Chronic lymphocytic leukemia) |
| CD22 (SIGLEC2) | Inotuzumab, tetraxetan, CAT-8015, DCDT2980S, Bectumomab | Chemotherapy-resistant hairy cell leukemia, Hodgkin's lymphoma |
| CD30 | Brentuximab vedotin | |
| CD33 | Gemtuzumab ozogamicin (Mylotarg) | Acute myeloid leukemia |
| CD37 | TRU-016 | Chronic lymphocytic leukemia |
| CD38 | Daratumumab | Multiple myeloma, hematological tumors |
| CD40 | Lucatumumab | Non-Hodgkin's lymphoma |
| CD52 | Alemtuzumab (Campath) | Chronic lymphocytic leukemia |
| CD56 (NCAM1) | Lorvotuzumab | Small Cell Lung Cancer |
| CD66e (CEA) | Labetuzumab | Breast, colon and lung tumors |
| CD70 | SGN-75 | Non-Hodgkin's lymphoma |
| CD74 | Milatuzumab | Non-Hodgkin's lymphoma |
| CD138 (SYND1) | BT062 | Multiple Myeloma |
| CD152 (CTLA-4) | Ipilimumab | Metastatic melanoma |
| CD221 (IGF1R) | AVE1642, IMC-A12, MK-0646, R150, CP 751871 | Glioma, lung, breast, head and neck, prostate and thyroid cancer |
| CD254 (RANKL) | Denosumab | Breast and prostate carcinoma |
| CD261 (TRAILR1) | Mapatumumab | Colon, lung and pancreas tumors and haematological malignancies |
| CD262 (TRAILR2) | HGS-ETR2, CS-1008 | |
| CD326 (Epcam) | Edrecolomab, 17-1A, IGN101, Catumaxomab, Adecatumumab | Colon and rectal cancer, malignant ascites, epithelial tumors (breast, colon, lung) |
| CD309 (VEGFR2) | IM-2C6, CDP791 | Epithelium-derived solid tumors |
| CD319 (SLAMF7) | HuLuc63 | Multiple myeloma |
| CD340 (HER2) | Trastuzumab, Pertuzumab, Ado-trastuzumab emtansine | Breast cancer |
| CAIX (CA9) | cG250 | Renal cell carcinoma |
| EGFR (c-erbB) | Cetuximab, Panitumumab, nimotuzumab and 806 | Solid tumors including glioma, lung, breast, colon, and head and neck tumors |
| EPHA3 (HEK) | KB004, IIIA4 | Lung, kidney and colon tumors, melanoma, glioma and haematological malignancies |
| Episialin | Epitumomab | Epithelial ovarian tumors |
| FAP | Sibrotuzumab and F19 | Colon, breast, lung, pancreas, and head and neck tumors |
| HLA-DR beta | Apolizumab | Chronic lymphocytic leukemia, non-Hodkin's lymphoma |
| FOLR-1 | Farletuzumab | Ovarian tumors |
| 5T4 | Anatumomab | Non-small cell lung cancer |
| GD3/GD2 | 3F8, ch14.18, KW-2871 | Neuroectodermal and epithelial tumors |
| gpA33 | huA33 | Colorectal carcinoma |
| GPNMB | Glembatumumab | Breast cancer |
| HER3 (ERBB3) | MM-121 | Breast, colon, lung, ovarian, and prostate tumors |
| Integrin αVβ3 | Etaracizumab | Tumor vasculature |
| Integrin α5β1 | Volociximab | Tumor vasculature |
| Lewis-Y antigen | hu3S193, IgN311 | Breast, colon, lung and prostate tumors |
| MET (HGFR) | AMG 102, METMAB, SCH900105 | Breast, ovary and lung tumors |
| Mucin-1/CanAg | Pemtumomab, oregovomab, Cantuzumab | Breast, colon, lung and ovarian tumors |
| PSMA | ADC, J591 | Prostate Cancer |
| Phosphatidylserine | Bavituximab | Solid tumors |
| TAG-72 | Minretumomab | Breast, colon and lung tumors |
| Tenascin | 81C6 | Glioma, breast and prostate tumours |
| VEGF | Bevacizumab | Tumour vasculature |

Accordingly, a cellular therapeutic that targets an expressed construct encoding a polypeptide antigen can be used in combination with one or more of these (or other) known antibodies.

The following examples are provided for illustrative purposes only and are not intended to limit the invention in any manner.

EXEMPLIFICATION

Example 1

An Antigen-activation Controlled Promoter Promotes Cytokine Release after Cellular Therapeutic Cells Encounter an Antigen (e.g., Tumor Cells or their Local Environment)

Cytokine support for cancer therapeutics has a long history (e.g. the systemic use of TNF, LTa, IFNa and IL-2). Inherent problems with systemic cytokine therapy include high dosage requirement, minimal efficacy, and toxicity (lethal in the case of TNF and LTa). Such toxicity limits the use of IL-12 and IL-15.

For example, systemic recombinant IL-12 induced multiple serious adverse effects, including renal and systemic toxicity. High-dose levels were linked to temporary immune suppression, which would be unfavorable for effective immunotherapy. (See, Leonard et al., *Blood* 1997; 90:2541-8, and Colombo, MP et al., *CytokineGrowth Factor Rev* 2002; 13:155-68, incorporated herein by reference. The majority of systemic IL-12 trials were associated with toxic adverse events and limited efficacy, since the cytokine did not reach the tumor site(s) in sufficient concentration (S Tugues, et al., 2015 *Cell Death Differ* 22: 237-246, incorporated herein by reference.

Recombinant IL-15 induces NK and CD8 cell mediated toxicities. Dose-limiting toxicities observed in patients receiving rIL-15 included grade 3 hypotension, thrombocytopenia, and elevations of ALT and AST, resulting in a suboptimal maximum-tolerated dose, having minimal clinical efficacy. (See, Conlon, K., et al., *J. of Clinical Oncology* Jan. 1, 2015: 74-82, incorporated herein by reference).

These and similar studies illustrate the dose-limiting toxicity and minimal efficacy associated with the uncontrolled administration and systemic distribution of cytokines. Accordingly, an individual with cancer or suspected of having cancer (e.g., tumor) is administered with a composition that allows for the direct transduction of the tumor cells so that a fusion protein of a cytokines and a target. The administration can be intravenously or intra-tumorally.

Example 2

Release of Cytokines from Transduced Tumor Cells

CAR T cells, CAR NK cells, TCR T cells, TIL, allogeneic NK cells and autologous NK cells are engineered for prolonged release of IL-21 as a cytokine fusion protein with TAA. Expansion and effector differentiation is induced in CD8+ T cells, and NK cell activation and cytolytic activity is supported.

Engagement of activation signals rapidly secretes IL-15 under the control of the TNF promoter, which supports NK cell expansion (e.g., CAR NK, allogeneic NK cells, and autologous NK cells) or recruits NK cell promulgation in an anti-tumor response (e.g., CAR T, TCR, TIL). Alternatively, various combinations of cytokines expressed and promoters are used, and are expressed in a suitable manner (IL-2, IL-12, IL-36g, IFNg) as a fusion protein.

Sustained local production of an anti-TAA scFv antibody fused to IL-12 recruits immune cells to support and expand the anti-tumor immune response triggered by engagement with the CAR T cell or other cellular therapeutic.

Example 3

The Targeting Method Utilizes a Single Chain Variable Fragment (scFv) Antibody (or Fragment thereof), or Secreted Heterodimer TCR Alpha/Beta or Gamma/Delta Chains are Fused to an Antibody-drug Conjugate Target The target is the polypeptide sequence, protein domain or domains recognized by the ADC, which is an antibody coupled to a toxin. ADC targets are the HER2 receptor, the CD30 cell surface protein, folate receptor alpha, and CD19, among many others.

The targeting method utilizes an scFv antibody or fragment thereof, and is fused to an antibody-drug conjugate target. Alternatively, a secreted heterodimer TCR alpha/beta or gamma/delta chain targeting method is used. Example antibody-drug conjugate target includes CD30, HER2, or ADCC antibody targets.

Example 4

The Targeting Method Utilizes a Single Chain Variable Fragment (scFv) Antibody (or Fragment thereof), or Secreted Heterodimer TCR Alpha/Beta or Gamma/Delta Chains are Fused to a Pro-immune Response Agent.

A "pro-immune response agent" is any agent capable of stimulating the immune response by stimulation cells comprising the immune response cell populations. Agents that stimulate immune responses directly include cytokines, the "danger signals" (DAMPS, PAMPs, TLR agonists etc.), agonist antibodies or ligands (e.g. anti-4-1BB, CD40L, B7-1, and many others), inhibitors of immunosuppressive signals (antagonists of PD-1, PD-L1, CTLA4, Lag-3, TIM-3, IDO1, adenosine receptor, TGFbeta, and many others)

The targeting method utilizes a scFv antibody (or fragment thereof), alternatively, the targeting method is a secreted heterodimer TCR alpha/beta or gamma/delta chain. In both targeting methods, the pro-immune response agent includes IL-2, IFNalpha, IL-12, IL-15, IL-21, any TLR agonist and any immune checkpoint antibody (or fragment thereof).

Example 5

The Targeting Method Utilizes a Single Chain Variable Fragment (scFv) Antibody (or Fragment thereof), or Secreted Heterodimer TCR Alpha/Beta or Gamma/Delta Chains Fused to Cell Recruiting Moieties.

Another method for recruitment of immune effector cells is the development of bipecific T-cell Engagers (e.g. BiTEs) which consist of two scFvs connected by a linker One arm is an anti-TAA scFv, and the second scFv binds to the CD3ε subunit of the TCR complex and therefore triggers T cell activation. Importantly, BiTEs and related molecules (DARTs, diabodies, fCabs etc) elicit repeated rounds of tumor cell lysis by T cells at very low effector/target (E/T) cell ratios. The cytotoxicity is mediated by membrane perforation and subsequent induction of granzymes and apoptosis, exactly the type of killing that one wished to elicit in the anti-tumor setting. Normally, the affinity of the anti-TAA scFv tumor-associated antigen is much higher than that directed against CD3—this enforces specificity for the targeted tumor. Many BiTEs have been generated, including BiTEs that target CD19, EpCAM, HER2, carcinoembryonic antigen (CEA), ephrin A2 (EphA2), CD33, and melanoma-associated chondroitin sulfate proteoglycan (MCSP). Other BiTEs that are in clinical studies are composed of EpCAM, prostate-specific membrane antigen (PSMA), or CEA-binding molecules combined with CD3-binding modules.

In some examples, the targeting method utilizes an scFv antibody (or fragment thereof), alternatively, the targeting method includes a secreted heterodimer TCR alpha/beta or gamma/delta chain. In both targeting methods, the cell recruiting moiety is fused to anti-CD16. In alternative examples, the cell recruiting moiety is fused to an anti-CD3 moiety, and utilizes the BiTE® technology described herein.

Example 6

Transfection of a Tumor in vivo using an HPV Pseudovirus with an ScFv-CD19 Fusion Protein in which the ScFv Binds the TAA Her2, and the Tumor is Killed by CD19-directed CART Cells HPV pseudovirus comprising an ScFv-CD19 fusion protein is injected IV to transduce tumor cells in a xenograft mouse model of breast cancer expressing Her2. The transduced tumors secrete the ScFv-CD19 fusion protein, resulting in coating of tumor cells with the ScFv-Cd19 fusion protein via ScFv binding to Her2. Addition of CD19-directed CAR T cells kills the tumor cells coated with CD19. CAR T cells directed to CD19 are made by standard methods.

Example 7

Transfection of a Tumor in vivo using an AAV-Phage Chimeric Virus with an ScFv-CD19 Fusion Protein in which the ScFv Binds the TAA Her2, and the Tumor is Killed by CD19-directed CAR T Cells.

A chimeric AAV/phage virus is injected IV to transduce tumor cells in a xenograft mouse model of breast cancer expressing Her2. The transduced tumors secrete the ScFv-CD19 fusion protein, resulting in coating of tumor cells with the ScFv-CD19 fusion protein via ScFv binding to Her2. Addition of CD19-directed CAR T cells kills the tumor cells coated with CD19. The generation of CD19 directed CAR T cells is well established.

Example 8

Transfection of a Tumor in vivo using an HPV Pseudovirus with an ScFv-CD30 Fusion Protein in which the ScFv Binds the TAA Her2, and the Tumor is Killed by a CD30-targeted ADC HPV pseudovirus comprising an ScFv-CD30 fusion protein is injected IV to transduce tumor cells in a xenograft mouse model of breast cancer expressing Her2. The transduced tumors secrete the ScFv-CD30 fusion protein, resulting in coating of tumor cells with the ScFv-CD30 fusion protein via ScFv binding to Her2. Addition of CD30-directed antibody-drug conjugate (ADC) kills the tumor cells coated with CD30. Adcetris is a commercially available ADC from Seattle Genetics.

Example 9

Transduction of Cells with AAV Viral Particles Encoding Fusion Proteins Results in Secreted Functional Fusion Proteins Capable of Directing CAR19 T Cell Targeting and Activation.

The present Example demonstrates expression of fusion proteins from cells transduced with AAV viral particles encoding fusion proteins. Further, the present example demonstrates that the expressed fusion proteins are capable of being bound by the anti-CD19 antibody FMC63 and detected by an anti-His antibody binding to the C-terminal His tag. Once expressed the fusion proteins are able to activate CAR19 T cells in the presence of cells that are CD19 negative.

The following table lists the various constructs tested in this example:

| Construct # | Description | Amino Acid SEQ ID NO: | Nucleotide SEQ ID NO: |
| --- | --- | --- | --- |
| 1 | CD19-D1 + 2-Trastuzumab scFv (VH/VL) | 1 | 2 |
| 3 | CD19 D1 + D2-MOC31 scFv (VH/VL) | 3 | 4 |
| 5 | CD19 D1 + D2-LY2875358 scFv (VH/VL) | 5 | 6 |
| 7 | CD19 D1 + D2-Panitumumab scFv (VH/VL) | 7 | 8 |

Methods

A 12 well plate was seeded with either A431 or 293T cells around 4×10e5 cells/well in DMEM+10% FBS media. The following day, one well was counted to get an accurate count for the viral infections. Cells were infected with a multiplicity of infection (MOI) of $1\times10^6$ or $5\times10^6$. AAV2 viral particles were made by Vigene (Rockville, Md.). The viral particles were generated from plasmids where the inserts containing the CD19 D1+D2-scFv-His sequences were cloned into pAV-FH. The viral particles AAV-1 (CD19-D1+ 2-Trastuzumab scFv (VH/VL), SEQ ID NO:1), AAV-3 (CD19 D1+D2-MOC31 scFv (VH/VL), SEQ ID NO:3), AAV-5 (CD19 D1+D2-LY2875358 scFv (VH/VL), SEQ ID NO:5) and AAV-7 (CD19 D1+D2-Panitumumab scFv (VH/VL), SEQ ID NO:7) had titers of $8.39\times10^{13}$, $1.51\times10^{14}$, $3.03\times10^{14}$ and $2.13\times10^{14}$ GC/ml, respectively. Infections were done in 0.6 ml/well DMEM+2% FBS where the virus was added directly into the media. Different concentrations of virus were used from $10^4$ (aka "104" or "10e4") to $5\times10^6$ (aka "5×106" or "5×10e6"). The following day, the media was changed to DMEM+10%FBS and the incubation continued for 3 or 6 days.

ELISA

Expression analysis was examined in the supernatant using an ELISA where anti-CD19 FMC63 was used for capture and anti-His used for detection. Briefly, 96 well plates (Pierce, Cat# 15041) were coated with 1.0 µg/ml reagent in 0.1 M carbonate, pH 9.5 for O/N at 4 C. The plates were then blocked with 0.3% nonfat dry milk (NFD) in TBS (200 µl/well) for 1 hr at RT. Plates were then washed 3× with wash buffer (1× TBST: 0.1 M Tris, 0.5 M NaCl, 0.05% Tween20). Titrations were performed from undiluted cell culture supernatant or purified protein at 1.0 µg/ml with serial 3× dilutions, 100 µl per well and incubate for 1 h at RT. Dilution buffer is 1% BSA in 1× TBS (0.1 M Tris, 0.5 M NaCl) followed by washing 3× with wash buffer. Secondary reagents were added (if needed) such as Biotinylated-reagents at 1 µg/ml concentration at RT for 1 hour. HRP-conjugated reagents were added at 1:2000, applied 100 µl per well, incubated at RT in dark for 1 hr. 100 µl 1-Step Ultra TMB-ELISA (Thermo Fisher, Prod#34028) was added per well. Plates were read at 405 nm when color had developed. XTT Cell Proliferation Assay (ATCC, Cat# 30-1011K)

Figure 2A:
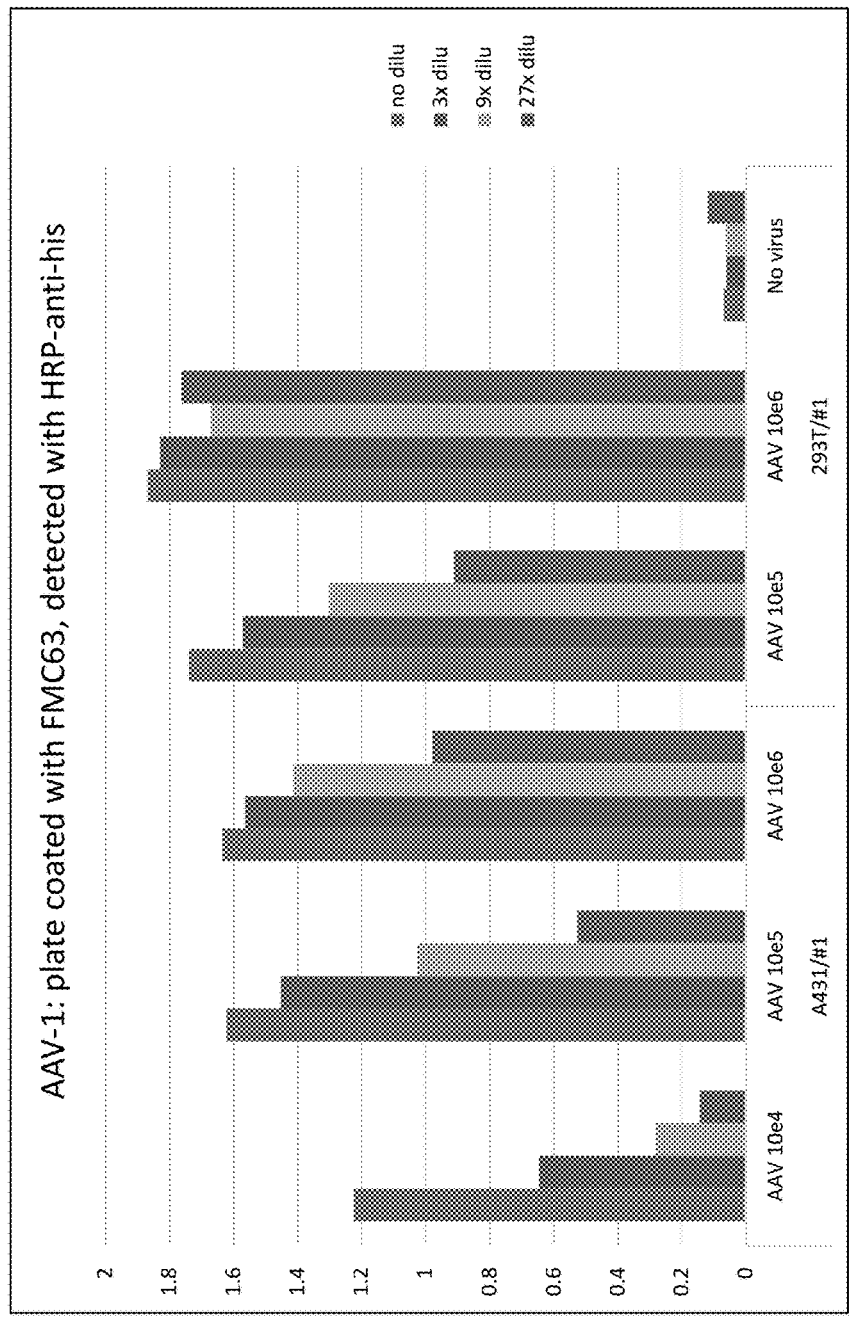
FIGS. 2A-2C demonstrate expression of fusion proteins from AAV transduced cells.
Figure 2B:
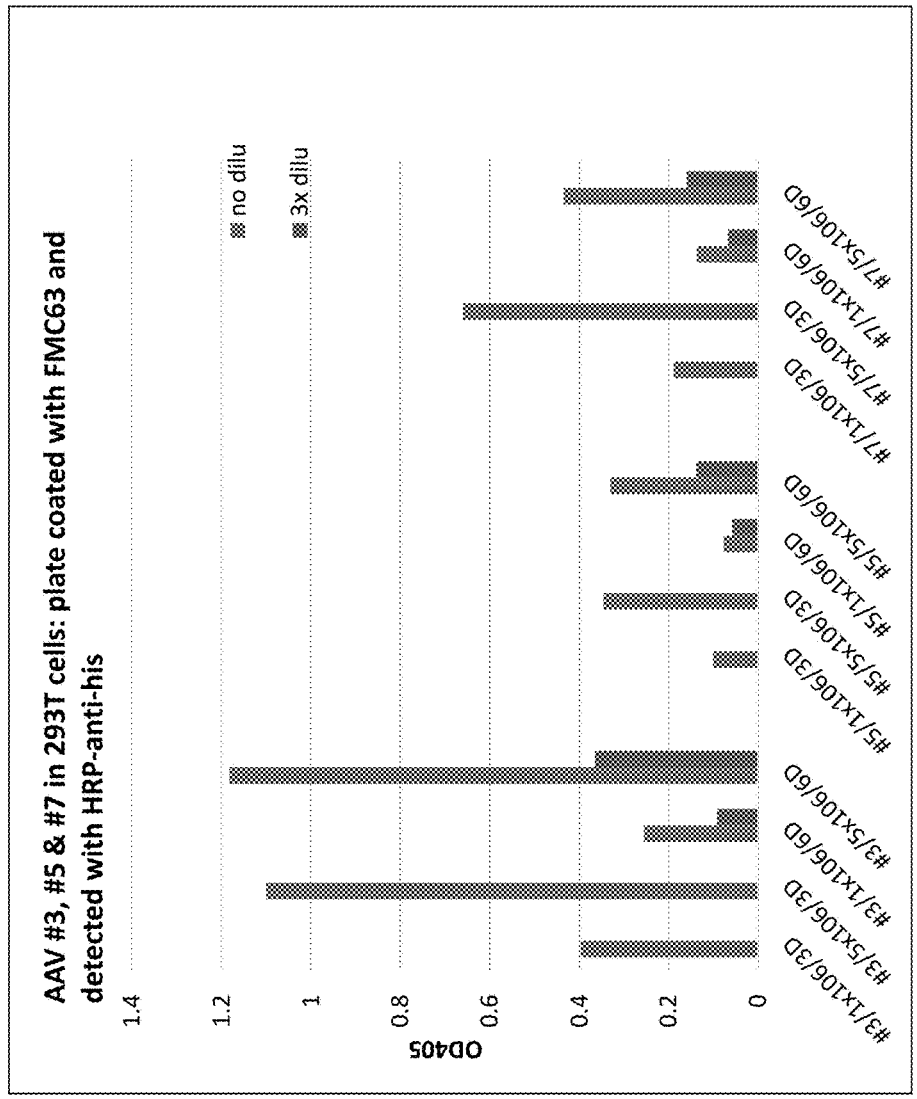
Figure 2C:
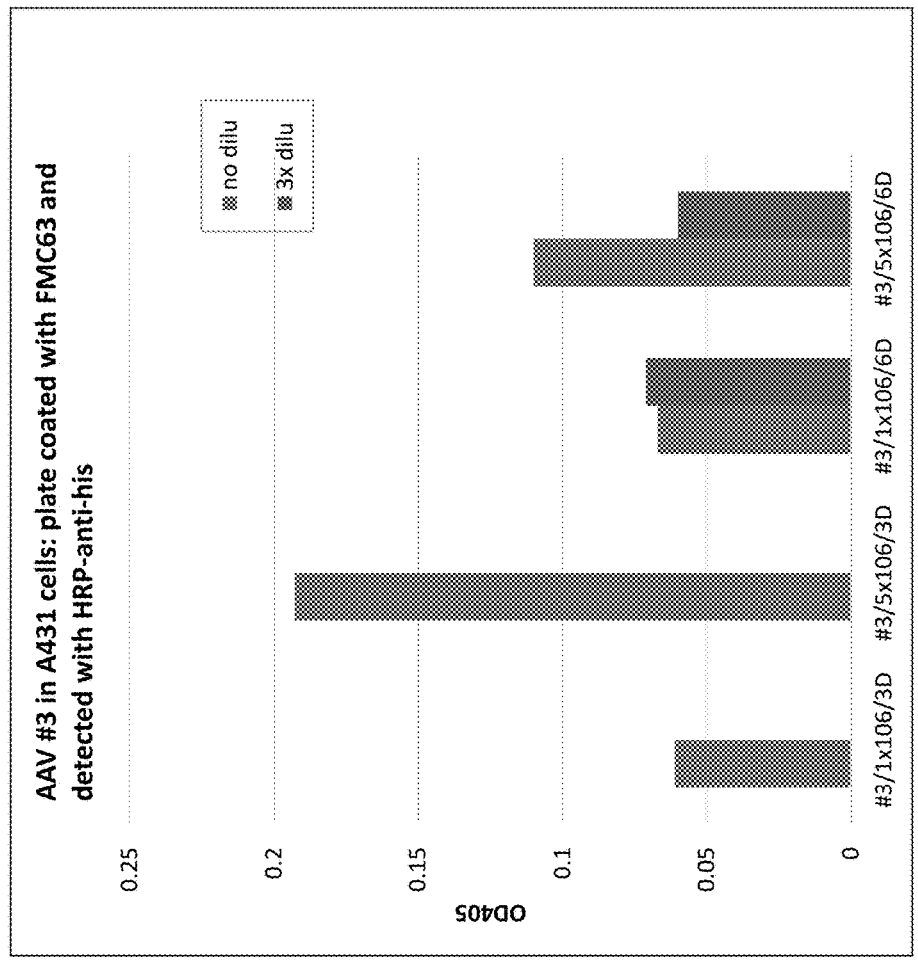

An aliquot of the XTT reagent and the activation reagent was rapidly thawed at 37oC prior to use. 0.1 ml of activation reagent was then added to 5.0 ml of the XTT reagent. 50 µl of the activated—XTT solution was then added to each well. The plate was placed in the cell culture incubator for 2-4 hours and monitored for color development. The absorbance of the plate was read at wavelength 450 nm. The % cell death (aka cytotoxicity) was calculated as follows: % killing=[1−OD(experimental wells−corresponding number of T cells)/OD (tumor cells without T cell-medium)]X100
Interferon Gamma Concentration Assay by ELISA A 96 well plate (Pierce, product #15041) was coated with 1.0 µg/ml mouse anti-human IFNγ (BD Pharmingen, Cat# 551221) in 0.1 M carbonate buffer, pH 9.5, overnight at 4° C. The plate was blocked with 0.3% non-fat dry milk solution in tris-buffered saline (TBS) using 200 µl/well for 1 hour at room temperature. The plate was washed ×3 with wash buffer (1× TBS/Tween: 0.1 M Tris, 0.5 M NaCl, 0.05% Tween20). 100 µl culture supernatant from the 24 hour or 48 hour culture plates (see above) were added to the ELISA plate. A titration of recombinant human IFNγ (Thermo Fisher, Cat# RIFNG100) was also performed in the same plate from 300 ng/ml with serial 3× dilutions to 2 pg/ml to generate a standard curve. The plate was then incubated for 1 hour at room temperature. The dilution buffer was 1× TBS (0.1 M Tris, 0.5 M NaCl) plus 1% BSA. The plate was washed ×3 with wash buffer. Biotinylated mouse anti-human IFNγ (BD Pharmingen, Cat# 554550) was added at 1 µg/ml concentration and the plate was incubated at room temperature for 1 hour. The plate was washed again ×3 with wash buffer. HRP-conjugated Streptavidin (Thermo Fisher, Cat# 21130) was added at a 1:2000 dilution from the stock, with 100 µl added per well. The plate was then incubated at room temperature for 1 hour in the dark. The plate was washed again ×3 with wash buffer. 100 µl per well of 1-Step Ultra TMB-ELISA development solution (Thermo Fisher, Cat #34028) was added per well. The plate was read at wavelength 405 nm when color developed sufficiently.
Results FIGS. 2A-2C demonstrate expression of fusion proteins from transduced cells. FIG. 2A shows detection of fusion protein CD19-D1+2-Trastuzumab scFv (VH/VL) (AAV#1) is expressed after transduction of A431 or 293T cells with AAV viral particles encoding the fusion protein. The expressed fusion protein is capable of being bound by the anti-CD19 antibody FMC63 and detected by an anti-His antibody binding to the C-terminal His tag. FIG. 2B demonstrates detection of expression of fusion proteins AAV-3 (CD19 D1+D2-MOC31 scFv (VH/VL), SEQ ID NO:3), AAV-5 (CD19 D1+D2-LY2875358 scFv (VH/VL), SEQ ID NO:5) and AAV-7 (CD19 D1+D2-Panitumumab scFv (VH/VL), SEQ ID NO:7) resulting from transduction of 293T cells with AAV particles encoding the indicated fusion protein. FIG. 2C demonstrates detection of expression of fusion protein AAV-3 (CD19 D1+D2-MOC31 scFv (VH/VL) resulting from transduction of A431 cells with AAV particles encoding the fusion protein.

Figures 3A, 3B:
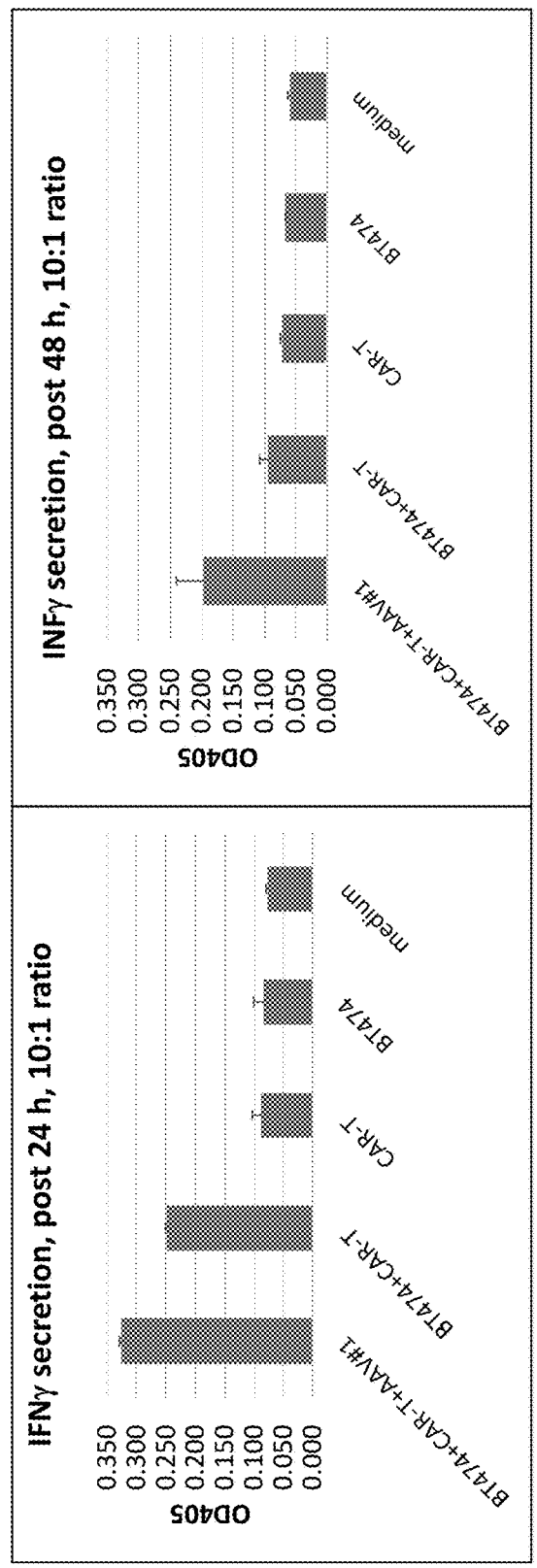
FIGS. 3A and 3B show summary results of an IFNγ ELISA measuring induction of IFNγ in CAR19 T-cells by expressed fusion proteins.

FIGS. 3A and 3B show a summary of results of the IFNγ ELISA measuring induction of IFNγ upon incubation of CAR19 T cells (Promab) with AAV-1-expressed supernatant and BT474 cells. FIG. 3A shows the results of the IFNγ ELISA at 24 hrs at a 10:1 effector:target ratio. FIG. 3B shows the results of the IFNγ ELISA at 48 hrs at a 10:1 effector:target ratio.

Figure 4A:
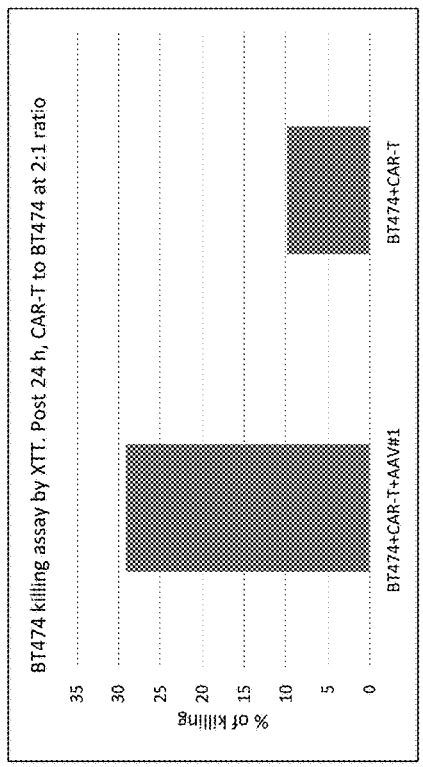
FIGS. 4A-4C show induction of cytotoxicity upon incubation of CAR19 T cells with AAV-1-expressed supernatant and BT474 cells.
Figure 4C:
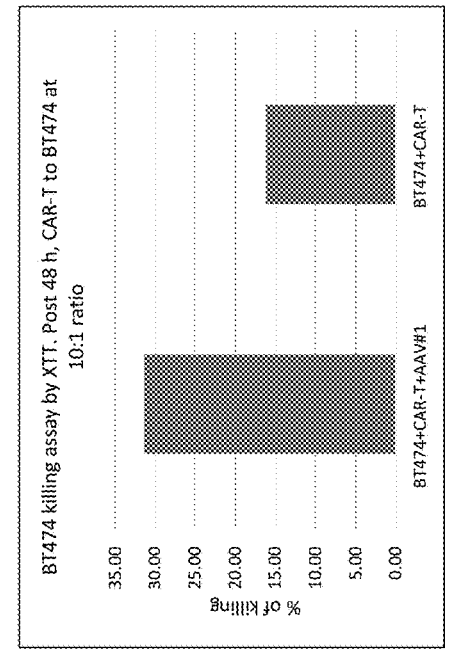
Figure 4B:
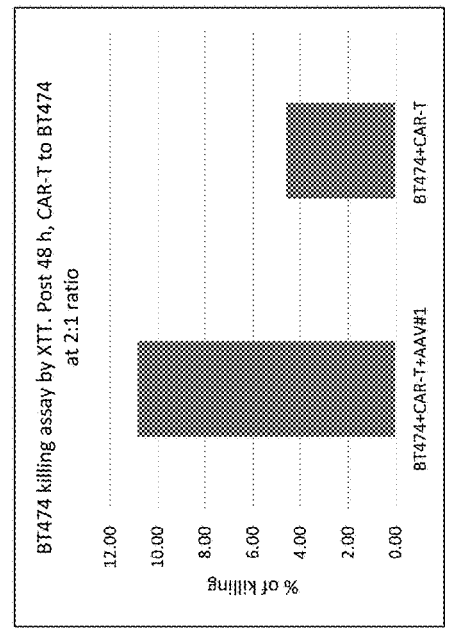

FIGS. 4A-4C show induction of cytotoxicity upon incubation of CAR19 T cells (Promab) with AAV-1-expressed supernatant and BT474 cells. FIG. 4A shows summary XTT-cytotoxicity results for 2:1 effector:target ratio after 24 hours. FIG. 4B shows summary XTT-cytotoxicity results for 2:1 effector:target ratio after 48 hours. FIG. 4C shows summary XTT-cytotoxicity results for 10:1 effector:target ratio after 48 hours. These results demonstrate that AAV transduction of cells (e.g. tumor cells) can result in expression of functional fusion proteins which can direct CAR19 T cell activation and cytotoxicity.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

What is claimed is:

1. An adenoviral vector, comprising a nucleotide sequence encoding a fusion protein comprising:
   (a) an antibody, or antigen-binding fragment thereof, that binds a tumor antigen; and
   (b) a polypeptide antigen wherein the polypeptide antigen:
      (i) is not a target antigen for endogenous immune cells in an individual; and
      (ii) is a target antigen for an administered therapeutic selected from the group consisting of: cellular therapeutics, antibodies, or antibody-drug conjugates.

2. The vector of claim 1, wherein the polypeptide antigen is a B cell antigen.

3. The vector of claim 2, wherein the B cell antigen is CD19 or CD22.

4. The vector of claim 1, wherein the tumor antigen is HER-2/neu, c-met, EGFR, Ga733\EpCAM, CD20, ROR1, or BCMA.

5. The vector of claim 1, wherein the antigen-binding fragment is an Fab, scFv, Fv, or VHH.

6. The vector of claim 1, wherein the cellular therapeutic is a CAR-T cell or CAR-NK cell.

7. A method of treating a subject having a tumor, comprising administering to the subject the adenoviral vector of claim 1.

8. An oncolytic viral vector, comprising a nucleotide sequence encoding a fusion protein comprising:
   (a) an antibody, or antigen-binding fragment thereof, that binds a tumor antigen; and
   (b) a polypeptide antigen wherein the polypeptide antigen:
      (i) is not a target antigen for endogenous immune cells in an individual; and
      (ii) is a target antigen for an administered therapeutic selected from the group consisting of: cellular therapeutics, antibodies, or antibody-drug conjugates.

9. The vector of claim 8, wherein the polypeptide antigen is a B cell antigen.

10. The vector of claim 9, wherein the B cell antigen is CD19 or CD22.

11. The vector of claim 8, wherein the tumor antigen is HER-2/neu, c-met, EGFR, Ga733\EpCAM, CD20, ROR1, or BCMA.

12. The vector of claim 8, wherein the antigen-binding fragment is an Fab, scFv, Fv, or VHH.

13. The vector of claim 8, wherein the cellular therapeutic is a CAR-T cell or CAR-NK cell.

14. The vector of claim 8, wherein the oncolytic viral vector is an autonomous parvoviral vector, myxoma viral vector, paramyxoviral vector, reoviral vector, picornaviral vector, vaccinia viral vector, adenoviral vector, herpes simplex viral vector, or a vesicular stomatitis viral vector.

15. A method of treating a subject having a tumor, comprising administering to the subject an oncolytic viral vector comprising a nucleotide sequence encoding a fusion protein comprising:
   (a) an antibody, or antigen-binding fragment thereof, that binds a tumor antigen; and
   (b) a polypeptide antigen wherein the polypeptide antigen:
      (i) is not a target antigen for endogenous immune cells in an individual; and
      (ii) is a target antigen for an administered therapeutic selected from the group consisting of: cellular therapeutics, antibodies, or antibody-drug conjugates.

16. The method of claim 15, wherein the polypeptide antigen is a B cell antigen.

17. The method of claim 16, wherein the B cell antigen is CD19 or CD22.

18. The method of claim 15, wherein the tumor antigen is HER-2/neu, c-met, EGFR, Ga733\EpCAM, CD20, ROR1, or BCMA.

19. The method of claim 15, wherein the antigen-binding fragment is an Fab, scFv, Fv, or VHH.

20. The method of claim 15, wherein the oncolytic viral vector transforms a tumor cell in the subject.

21. The method of claim 20, wherein the transformed tumor cell secretes the fusion protein.

22. The method of claim 21, wherein the fusion protein binds a tumor antigen on the transformed tumor cell.

23. The method of claim 21, wherein the fusion protein binds a tumor antigen on a non-transformed tumor cell.

24. The method of claim 15, wherein the cellular therapeutic is a CAR-T cell or CAR-NK cell.

25. The method of claim 24, further comprising administering the cellular therapeutic to the subject.

26. The method of claim 25, wherein upon administration, the cellular therapeutic binds to the fusion protein.

27. The method of claim 26, wherein binding of the cellular therapeutic to the fusion protein induces killing of the tumor.

28. The method of claim 15, wherein the oncolytic viral vector is an autonomous parvoviral vector, myxoma viral vector, paramyxoviral vector, reoviral vector, picornaviral vector, vaccinia viral vector, adenoviral vector, herpes simplex viral vector, or a vesicular stomatitis viral vector.

* * * * *